(12) United States Patent  
Burkholz et al.

(10) Patent No.: US 12,097,343 B2  
(45) Date of Patent: Sep. 24, 2024

(54) SYSTEMS AND METHODS TO IMPROVE INSTRUMENT GUIDANCE WITHIN AN INTRAVENOUS CATHETER ASSEMBLY

(71) Applicant: Becton, Dickinson and Company, Franklin Lakes, NJ (US)

(72) Inventors: Jonathan Karl Burkholz, Salt Lake City, UT (US); Curtis H. Blanchard, Riverton, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 103 days.

(21) Appl. No.: 17/379,416

(22) Filed: Jul. 19, 2021

(65) Prior Publication Data

US 2021/0346653 A1 Nov. 11, 2021

Related U.S. Application Data

(63) Continuation of application No. 16/110,863, filed on Aug. 23, 2018, now Pat. No. 11,097,083, which is a
(Continued)

(51) Int. Cl.
| | |
|---|---|
| *A61M 25/06* | (2006.01) |
| *A61M 5/32* | (2006.01) |
| *A61M 25/00* | (2006.01) |

(52) U.S. Cl.
CPC .... *A61M 25/0606* (2013.01); *A61M 25/0097* (2013.01); *A61M 25/0662* (2013.01);
(Continued)

(58) Field of Classification Search
CPC .......... A61M 25/0606; A61M 25/0097; A61M 25/0662; A61M 25/0693; A61M 5/3275;
(Continued)

(56) References Cited

U.S. PATENT DOCUMENTS

| | | | |
|---|---|---|---|
| 2,961,682 | A | 11/1960 | Wurmbock et al. |
| 3,863,632 | A | 2/1975 | Schwarts |

(Continued)

FOREIGN PATENT DOCUMENTS

| | | |
|---|---|---|
| CA | 2865175 A1 | 8/2013 |
| CN | 101077433 A | 11/2007 |

(Continued)

OTHER PUBLICATIONS

Corrected Petition for Inter Partes Review Under 35 U.S.C . . . sctn . . . sctn. 311-319 and 37 C.F.R . . . sctn. 42,100 et seq., USPTO, Patent Trial and Appeal Board, *Excelsior Medical Corporation v. Becton, Dickinson and Company*, Case PR2014-00880, U.S. Pat. No. 8,740,864, pp. 1-48, Jun. 23, 2014.

(Continued)

*Primary Examiner* — James D Ponton  
(74) *Attorney, Agent, or Firm* — Kirton McConkie; Whitney Blair; Kevin Stinger

(57) ABSTRACT

A system for facilitating instrument delivery through a peripheral intravenous catheter ("PIVC") may include a catheter assembly having a catheter adapter, an extension tube extending from a side port of the catheter adapter, a septum disposed in a lumen of the catheter adapter, and a PIVC extending distally from the catheter adapter. The septum may include a first piece and a second piece and may be least partially disposed within a canister. The system may include an extension set, which may include a distal end and a proximal end. The distal end may include a distal connector and a rigid tube. The proximal end may include a proximal connector. The distal connector may be coupled to the proximal end of the catheter adapter. The rigid tube may penetrate the septum in response to the distal connector being coupled to the proximal end of the catheter adapter.

19 Claims, 16 Drawing Sheets

Related U.S. Application Data continuation-in-part of application No. 16/037,274, filed on Jul. 17, 2018, now Pat. No. 11,147,957.

(52) U.S. Cl.
CPC ....... *A61M 25/0693* (2013.01); *A61M 5/3275* (2013.01); *A61M 2025/0675* (2013.01); *A61M 2025/0681* (2013.01)

(58) Field of Classification Search
CPC .. A61M 2025/0675; A61M 2025/0681; A61M 39/26; A61M 2039/062; A61M 2039/064; A61M 25/0111; A61M 39/06; A61M 39/162

See application file for complete search history.

(56) References Cited

U.S. PATENT DOCUMENTS

| | | | |
|---|---|---|---|
| 4,280,632 A | 7/1981 | Yuhara | |
| 4,282,891 A | 8/1981 | Duceppe | |
| 4,354,490 A | 10/1982 | Rogers | |
| 4,417,890 A | 11/1983 | Dennehey et al. | |
| 4,432,764 A | 2/1984 | Lopez | |
| 4,440,207 A | 4/1984 | Genatempo et al. | |
| 4,444,310 A | 4/1984 | Odell | |
| 4,531,937 A | 7/1985 | Yates | |
| 4,584,192 A | 4/1986 | Dell et al. | |
| 4,624,664 A | 11/1986 | Peluso et al. | |
| 4,655,762 A | 4/1987 | Rogers | |
| 4,671,306 A | 6/1987 | Spector | |
| 4,716,032 A | 12/1987 | Westfall et al. | |
| 4,753,358 A | 6/1988 | Virca et al. | |
| 4,778,447 A | 10/1988 | Velde et al. | |
| 4,915,934 A | 4/1990 | Tomlinson | |
| 4,925,668 A | 5/1990 | Khan et al. | |
| 4,989,733 A | 2/1991 | Patry | |
| 4,991,629 A | 2/1991 | Ernesto et al. | |
| 5,023,082 A | 6/1991 | Friedman et al. | |
| 5,135,489 A * | 8/1992 | Jepson | A61M 39/14 604/905 |
| 5,195,957 A | 3/1993 | Tollini | |
| 5,242,425 A | 9/1993 | White et al. | |
| 5,334,388 A | 8/1994 | Hoang et al. | |
| 5,335,373 A | 8/1994 | Dangman et al. | |
| 5,507,728 A | 4/1996 | Erskine | |
| 5,507,733 A * | 4/1996 | Larkin | A61M 39/1011 604/905 |
| 5,512,199 A | 4/1996 | Khan et al. | |
| 5,547,662 A | 8/1996 | Khan et al. | |
| 5,554,106 A | 9/1996 | Layman-Spillar et al. | |
| 5,569,207 A | 10/1996 | Gisselberg | |
| 5,616,338 A | 4/1997 | Fox, Jr. et al. | |
| 5,620,424 A | 4/1997 | Abramson | |
| 5,639,310 A | 6/1997 | Giampaolo, Jr. | |
| 5,641,464 A | 6/1997 | Briggs, III et al. | |
| 5,686,096 A | 11/1997 | Khan et al. | |
| 5,694,978 A | 12/1997 | Heilmann et al. | |
| 5,695,474 A | 12/1997 | Daugherty | |
| 5,702,017 A | 12/1997 | Goncalves | |
| 5,722,537 A | 3/1998 | Sigler | |
| 5,743,884 A | 4/1998 | Hasson et al. | |
| 5,861,440 A | 1/1999 | Gohla et al. | |
| 5,954,957 A | 9/1999 | Chin-Loy et al. | |
| 5,989,229 A | 11/1999 | Chiappetta | |
| 6,051,609 A | 4/2000 | Yu et al. | |
| 6,116,468 A | 9/2000 | Nilson | |
| 6,117,114 A | 9/2000 | Paradis | |
| 6,196,998 B1 | 3/2001 | Jansen et al. | |
| 6,213,978 B1 * | 4/2001 | Voyten | A61M 25/0631 604/164.01 |
| 6,227,391 B1 | 5/2001 | King | |
| 6,337,357 B1 | 1/2002 | Fukunishi et al. | |
| 6,413,539 B1 | 7/2002 | Shalaby | |
| 6,488,942 B1 | 12/2002 | Ingemann | |
| 6,523,686 B1 | 2/2003 | Bae | |
| RE38,145 E | 6/2003 | Lynn | |
| 6,708,363 B2 | 3/2004 | Larsen | |
| 6,846,846 B2 | 1/2005 | Modak et al. | |
| 6,861,060 B1 | 3/2005 | Luriya et al. | |
| 6,911,025 B2 | 6/2005 | Miyahara | |
| 6,994,315 B2 | 2/2006 | Ryan et al. | |
| 7,083,605 B2 | 8/2006 | Miyahara | |
| 7,198,800 B1 | 4/2007 | Ko | |
| 7,268,165 B2 | 9/2007 | Greten et al. | |
| 7,682,561 B2 | 3/2010 | Davis et al. | |
| 7,704,935 B1 | 4/2010 | Davis et al. | |
| 7,828,186 B2 | 11/2010 | Wales | |
| 7,922,701 B2 | 4/2011 | Buchman | |
| 8,065,773 B2 | 11/2011 | Vaillancourt et al. | |
| 8,113,731 B2 | 2/2012 | Cable, Jr. et al. | |
| 9,039,989 B2 | 5/2015 | Liu et al. | |
| 9,283,369 B2 | 3/2016 | Ma et al. | |
| 9,399,125 B2 | 7/2016 | Burkholz | |
| 9,480,833 B2 | 11/2016 | Hoang et al. | |
| 9,545,495 B2 | 1/2017 | Goral et al. | |
| 9,895,524 B2 | 2/2018 | Lareau | |
| 2001/0016589 A1 | 8/2001 | Modak et al. | |
| 2001/0053895 A1 | 12/2001 | Vaillancourt | |
| 2002/0045643 A1 | 4/2002 | Muller et al. | |
| 2002/0045843 A1 | 4/2002 | Barker et al. | |
| 2002/0144705 A1 | 10/2002 | Brattesani et al. | |
| 2002/0177814 A1 * | 11/2002 | Meng | A61M 39/045 604/164.07 |
| 2002/0193752 A1 | 12/2002 | Lynn | |
| 2003/0072781 A1 | 4/2003 | Pelerin | |
| 2003/0109853 A1 | 6/2003 | Harding et al. | |
| 2003/0153865 A1 | 8/2003 | Connell et al. | |
| 2003/0162839 A1 | 8/2003 | Symington et al. | |
| 2004/0004019 A1 | 1/2004 | Busch | |
| 2004/0039349 A1 | 2/2004 | Modak et al. | |
| 2004/0258560 A1 | 12/2004 | Lake, Jr. et al. | |
| 2005/0124970 A1 | 6/2005 | Kunin et al. | |
| 2005/0147524 A1 | 7/2005 | Bousquet | |
| 2005/0147525 A1 | 7/2005 | Bousquet | |
| 2005/0222542 A1 | 10/2005 | Burkholz et al. | |
| 2006/0015086 A1 * | 1/2006 | Rasmussen | A61M 25/0097 604/533 |
| 2006/0030827 A1 | 2/2006 | Raulerson et al. | |
| 2006/0135962 A1 * | 6/2006 | Kick | A61M 29/02 606/191 |
| 2006/0165751 A1 | 7/2006 | Chudzik et al. | |
| 2006/0239954 A1 | 10/2006 | Sancho | |
| 2007/0112333 A1 | 5/2007 | Hoang et al. | |
| 2007/0202177 A1 | 8/2007 | Hoang | |
| 2007/0225648 A1 * | 9/2007 | Winsor | A61M 39/10 604/905 |
| 2007/0225660 A1 | 9/2007 | Lynn | |
| 2007/0282280 A1 | 12/2007 | Tennican | |
| 2008/0019889 A1 | 1/2008 | Rogers et al. | |
| 2008/0027399 A1 | 1/2008 | Harding et al. | |
| 2008/0033371 A1 | 2/2008 | Updegraff et al. | |
| 2008/0075761 A1 | 3/2008 | Modak et al. | |
| 2008/0086091 A1 | 4/2008 | Anderson et al. | |
| 2008/0147047 A1 | 6/2008 | Davis et al. | |
| 2008/0177250 A1 | 7/2008 | Howlett et al. | |
| 2008/0182921 A1 | 7/2008 | Suh et al. | |
| 2009/0008393 A1 | 1/2009 | Howlett et al. | |
| 2009/0028750 A1 | 1/2009 | Ryan | |
| 2009/0028756 A1 | 1/2009 | Shahriari | |
| 2009/0062766 A1 | 3/2009 | Howlett et al. | |
| 2009/0149818 A1 | 6/2009 | Timm | |
| 2009/0149819 A1 | 6/2009 | Chelak | |
| 2009/0281556 A1 | 11/2009 | Newell et al. | |
| 2010/0000040 A1 | 1/2010 | Shaw et al. | |
| 2010/0047123 A1 | 2/2010 | Solomon et al. | |
| 2010/0049170 A1 | 2/2010 | Solomon et al. | |
| 2010/0050351 A1 | 3/2010 | Colantonio et al. | |
| 2010/0172794 A1 | 7/2010 | Ferlic et al. | |
| 2010/0204648 A1 | 8/2010 | Stout et al. | |
| 2010/0204652 A1 | 8/2010 | Morrissey et al. | |
| 2010/0292656 A1 | 11/2010 | Groskopf et al. | |
| 2010/0292673 A1 | 11/2010 | Korogi et al. | |
| 2011/0150958 A1 | 6/2011 | Davis et al. | |

(56) References Cited

U.S. PATENT DOCUMENTS

| | | |
|---|---|---|
| 2011/0160662 A1 | 6/2011 | Stout et al. |
| 2011/0265825 A1 | 11/2011 | Rogers et al. |
| 2012/0039765 A1 | 2/2012 | Solomon et al. |
| 2012/0197200 A1 | 8/2012 | Belson |
| 2012/0302997 A1 | 11/2012 | Gardner et al. |
| 2013/0090607 A1* | 4/2013 | McKinnon ........ A61M 39/0693 604/247 |
| 2013/0165867 A1* | 6/2013 | Isaacson ........... A61M 39/0606 604/534 |
| 2013/0310751 A1 | 11/2013 | Davis et al. |
| 2013/0331799 A1 | 12/2013 | Dasbach et al. |
| 2014/0135703 A1* | 5/2014 | Yeh .................. A61M 25/0693 604/533 |
| 2014/0163516 A1 | 6/2014 | Lareau |
| 2014/0350485 A1* | 11/2014 | Sonderegger ....... B29C 45/1657 604/533 |
| 2014/0364809 A1* | 12/2014 | Isaacson ........... A61M 25/0097 604/164.08 |
| 2015/0343179 A1 | 12/2015 | Schumacher |
| 2015/0360005 A1 | 12/2015 | Cabrera et al. |
| 2015/0374931 A1 | 12/2015 | Sugiki et al. |
| 2016/0106970 A1 | 4/2016 | Fangrow |
| 2016/0184558 A1 | 6/2016 | Raulerson et al. |
| 2016/0331937 A1 | 11/2016 | Teoh |

FOREIGN PATENT DOCUMENTS

| | | |
|---|---|---|
| CN | 101316621 A | 12/2008 |
| CN | 103285450 | 9/2013 |
| CN | 203525076 U | 4/2014 |
| EP | 1649890 A1 | 4/2006 |
| EP | 2606930 A1 | 6/2013 |
| EP | 2952220 | 12/2015 |
| JP | H10507946 A | 8/1998 |
| JP | 2001258713 A | 9/2001 |
| JP | 2002503968 A | 2/2002 |
| JP | 2016005807 A | 1/2016 |
| JP | 5867703 B2 | 2/2016 |
| JP | 2017503598 A | 2/2017 |
| WO | 8700441 A1 | 1/1987 |
| WO | 9929173 A1 | 6/1999 |
| WO | 2007044760 A2 | 4/2007 |
| WO | 2008157092 A1 | 12/2008 |
| WO | 2010039171 A1 | 4/2010 |
| WO | 2010143693 A1 | 12/2010 |
| WO | 2011053924 A1 | 5/2011 |
| WO | 2011066586 A1 | 6/2011 |
| WO | 2011115048 A1 | 9/2011 |
| WO | 2012133428 A1 | 10/2012 |
| WO | 2013047205 A1 | 4/2013 |
| WO | 2017/074677 | 5/2017 |
| WO | 2017074675 A1 | 5/2017 |
| WO | 2018/067161 | 4/2018 |
| WO | 2019018479 A1 | 1/2019 |

OTHER PUBLICATIONS

Decision, Institution of Inter Partes Review, 37 C.F.R . . . sctn. 42,108, USPTO, Patent Trial and Appeal Board, *Excelsior Medical Corporation v. Becton, Dickinson and Company*, Case IPR2014-00880, U.S. Pat. No. 8,740,864, pp. 1-21, Nov. 25, 2014.

Patent Owner's Preliminary Response Under 37 C.F.R . . . sctn. 42,10, USPTO, Patent Trial and Appeal Board, *Excelsior Medical Corporation v. Becton, Dickinson and Company*, Case IPR2014-00880, U.S. Pat. No. 8,740,864, pp. 1-30, Sep. 16, 2014.

\* cited by examiner

SYSTEMS AND METHODS TO IMPROVE INSTRUMENT GUIDANCE WITHIN AN INTRAVENOUS CATHETER ASSEMBLY

CROSS-REFERENCE TO RELATED APPLICATIONS

This application is a continuation of U.S. patent application Ser. No. 16/110,863, filed Aug. 23, 2018, entitled SYSTEMS AND METHODS TO IMPROVE INSTRUMENT GUIDANCE WITHIN AN INTRAVENOUS CATHETER ASSEMBLY, which is a continuation-in-part of U.S. patent application Ser. No. 16/037,274, filed Jul. 17, 2018, entitled SYSTEMS AND METHODS TO IMPROVE INSTRUMENT GUIDANCE WITHIN AN INTRAVENOUS CATHETER ASSEMBLY, which is incorporated herein in its entirety.

BACKGROUND OF THE INVENTION

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using a peripheral IV catheter may be difficult for several reasons, particularly when an indwelling time of the catheter is more than one day. For example, when the catheter is left inserted in the patient for a prolonged period of time, the catheter may be more susceptible to narrowing, collapse, kinking, blockage by debris (e.g., fibrin or platelet clots), and adhering of a tip of the catheter to the vasculature. Due to this, catheters may often be used for acquiring a blood sample at a time of catheter placement but are much less frequently used for acquiring a blood sample during the catheter dwell period. Therefore, when a blood sample is required, an additional needle stick may be needed to provide vein access for blood collection, which may be painful for the patient and result in higher material costs. Accordingly, there is a need for catheter systems and methods that facilitate placement of blood sample instruments, such as, for example, catheters, and probe instruments in the vasculature of the patient without additional needle sticks.

BRIEF SUMMARY OF THE INVENTION

The present application relates generally to instrument guidance within a catheter system, which may include a peripheral IV catheter system. In some embodiments, the catheter system may include a catheter assembly. In some embodiments, the catheter assembly may include one or more of the following: a catheter, a catheter adapter, a septum housing, and a septum.

In some embodiments, the catheter adapter may include a distal end, a proximal end, and a lumen extending therebetween. In some embodiments, the septum may be disposed within the lumen of the catheter adapter. In some embodiments, the septum may be at least partially disposed within the septum housing and configured to at least substantially seal the lumen of the catheter adapter. In some embodiments, the septum housing may prevent dislodgement or destabilization of the septum, thereby preventing leakage of fluid from the lumen of the catheter adapter.

In some embodiments, the catheter assembly may be part of a closed IV catheter system or a catheter system with an integrated extension tube, such as, for example, the Becton Dickinson NEXIVA™ Closed IV Catheter System, the Becton Dickinson NEXIVA™ DIFFUSICS™ Closed IV Catheter System, or the Becton Dickinson PEGASUS™ Safety Closed IV Catheter System. In these and other embodiments, a proximal end of the catheter adapter may include a first port and a second port. In these and other embodiments, the lumen of the catheter adapter may include a first lumen and/or a second lumen. In some embodiments, the first port may form the first lumen and/or the second port may form the second lumen. In some embodiments, the first and second lumens may join at a common lumen. In some embodiments, the first lumen may be generally aligned with the common lumen and/or the second port may include a side port. In some embodiments, the septum and/or the septum housing may be disposed in the first lumen.

In the closed IV catheter system, an introducer needle may be withdrawn through the catheter adapter after insertion of the catheter into vasculature of a patient. In the closed IV catheter system, when the introducer needle is withdrawn through the catheter adapter, the first lumen, which may correspond to a "needle channel," may be closed off by the septum from an external environment surrounding the catheter adapter. Thus, the septum may at least substantially seal the first port and prevent fluid from exiting the catheter adapter through the first port. In some embodiments, a fluid pathway of the catheter assembly during fluid infusion and/or blood withdrawal may extend through the second port and not the first port.

In some embodiments, the second lumen of the catheter adapter may be connectable to blood withdrawal or infusion means via an extension tube that may extend from the second port of the catheter adapter. In some embodiments, the septum and/or the septum housing may be disposed proximal to the second port of the catheter adapter. In some embodiments, the catheter assembly may be part of another type of catheter system, such as, for example, a non-integrated catheter system or a catheter system without the integrated extension tube.

In some embodiments, the instrument may include another catheter or a probe. In some embodiments, the instrument may include a variable diameter along a length of the instrument. In some embodiments, the instrument may be guided by one or more features of the catheter system, such as, for example, one or more tapered surfaces, to allow the instrument to access a fluid pathway of the catheter assembly and/or the vasculature of the patient. In some embodiments, one or more features of the catheter system may guide the instrument through the septum to access the fluid pathway. In some embodiments, by accessing the fluid pathway and/or the vasculature through the septum, insertion of the instrument through a long and tortuous path of an integrated extension set may be avoided.

In some embodiments, the septum may include a proximal surface that is tapered inwardly in a distal direction such that the proximal surface is configured to guide an instrument distally through the septum. In some embodiments, the septum may include a cavity. In some embodiments, a distal end of the cavity may include an annular protrusion, which may form the proximal surface of the septum. In some embodiments, the septum may include a slit disposed at or near a center of or within the annular protrusion. In some embodiments, the proximal surface of the septum may include an inner surface of the septum or a surface of the septum disposed towards the slit of the septum.

In some embodiments, the septum housing may include a proximal surface that is tapered inwardly in the distal direction such that the proximal surface of the septum housing is configured to guide the instrument distally through the septum. In some embodiments, the septum housing may include a distal end and a proximal end. In some embodiments, the septum may be disposed at least partially within the distal end of the septum housing. In some embodiments, the proximal end of the septum housing may include the proximal surface of the septum housing. In some embodiments, the septum housing may include a canister.

In some embodiments, the catheter system may include an extension or introducer, which may be configured to introduce the instrument into the catheter assembly. In some embodiments, the introducer may include an introducer element, which may be coupled with the proximal end of the catheter adapter. In some embodiments, a proximal end of the introducer element may include an opening being at least partially formed by a proximal and/or an inner surface. In some embodiments, the inner surface may be tapered inwardly in the distal direction such that the inner surface is configured to guide the instrument distally through the introducer element and into the proximal end of the catheter adapter.

In some embodiments, the proximal end of the introducer element may include a coupling mechanism. In some embodiments, a distal end of the introducer element may include a tube or tubular element. In some embodiments, in response to the introducer being coupled to the catheter adapter via the coupling mechanism, the tube may penetrate the septum and/or extend proximate a proximal face of septum, which may help guide the instrument within the catheter assembly. In some embodiments, a distal end of the tube may be blunt, which may prevent harm to the septum.

In some embodiments, the introducer may include a cover disposed over top or at least partially covering the tube. In some embodiments, the cover may contact the proximal face of the septum. In some embodiments, the cover may be elastomeric. In some embodiments, the cover may include a slit, which may facilitate penetration of the cover by the instrument. In some embodiments, the slit of the cover may be aligned with the slit of the septum. In some embodiments, the cover may include one or more antimicrobial agents. In some embodiments, the cover may be configured to seal the introducer from any fluid leakage through the septum when the septum is closed.

In some embodiments, the introducer may include a sheath or sleeve, which may be coupled to the introducer element. In some embodiments, the sleeve may surround the instrument, which may protect the instrument from the external environment surrounding the introducer. In some embodiments, the instrument may be at least partially disposed within the sleeve. In some embodiments, the instrument may be advanced to a position beyond a distal end of the sleeve when the sleeve is compressed or collapsed in the distal direction. In some embodiments, the introducer may include a grip, which may be coupled to a proximal end of the sleeve. In some embodiments, a clinician may move the grip distally to compress or collapse the sleeve in the distal direction and advance the instrument to the position beyond the distal end of the sleeve. In some embodiments, the coupling mechanism may be coupled to a particular port of the catheter adapter. In some embodiments, the fluid may be prevented by the septum from exiting the catheter adapter via the particular port. In some embodiments, the sleeve may be at least partially disposed in a housing, as will be described in further detail.

In some embodiments, a system for facilitating instrument delivery through a peripheral intravenous catheter may include a catheter assembly. In some embodiments, the catheter assembly may include a catheter adapter, which may include a proximal end, a distal end, and a lumen extending therethrough. In some embodiments, the catheter adapter may include a side port. In some embodiments, an extension tube may extend distally from the side port.

In some embodiments, a septum may be disposed in the lumen of the catheter adapter. In some embodiments, the septum may include a first piece and a second piece. In some embodiments, the septum may be at least partially disposed within a canister. In some embodiments, a peripheral intravenous catheter may extend distally from the catheter adapter.

In some embodiments, an extension set may include a distal end and a proximal end. In some embodiments, the extension set may include an anti-reflux valve. In some embodiments, the distal end may include a distal connector and a rigid tube. In some embodiments, the distal connector may be coupled to the proximal end of the catheter adapter. In some embodiments, the rigid tube may penetrate the septum in response to the distal connector being coupled to the proximal end of the catheter adapter. In some embodiments, the rigid tube may be constructed of plastic or metal. In some embodiments, a distal end of the rigid tube may be blunt. In some embodiments, the rigid tube may include one or more flushing windows.

In some embodiments, the proximal end may include a proximal connector. In some embodiments, a needleless connector may be coupled to the proximal connector. In some embodiments, the extension set may include tubing disposed between the distal connector and the proximal connector. In some embodiments, the system may include an instrument disposed within the extension set and the catheter assembly. In some embodiments, the instrument may include a guidewire, a probe with a sensor, tubing for fluid infusion or blood draw, or a light tube for disinfection.

In some embodiments, the distal connector may include a non-luer adapter. In some embodiments, the distal connector may be coupled to the proximal end of the catheter adapter with a snap-fit. In some embodiments, the distal connector may be coupled to the proximal end of the catheter adapter with a press-fit. In some embodiments, the distal connector may include a distally-extending arm that contacts an outer surface of the catheter adapter. In some embodiments, the distally-extending arm may be locked to the outer surface of the catheter adapter. In some embodiments, the distal connector may include one or more wings, which may be configured to contact skin of a patient and stabilize the system against skin of a patient.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention. Moreover, the Figures may show simplified or partial views, and the dimensions of elements in the Figures may be exaggerated or otherwise not in proportion for clarity.

As used in the present disclosure, the terms "proximal" and "distal" may refer to the direction closer to and away from, respectively, a clinician who would place the catheter system into contact with a patient. Thus, for example, the end of the catheter system first touching the body of the patient would be the distal end, while the opposite end of the catheter system (e.g., the end of the device being manipulated by the clinician) would be the proximal end of the catheter system.

Figure 1A:
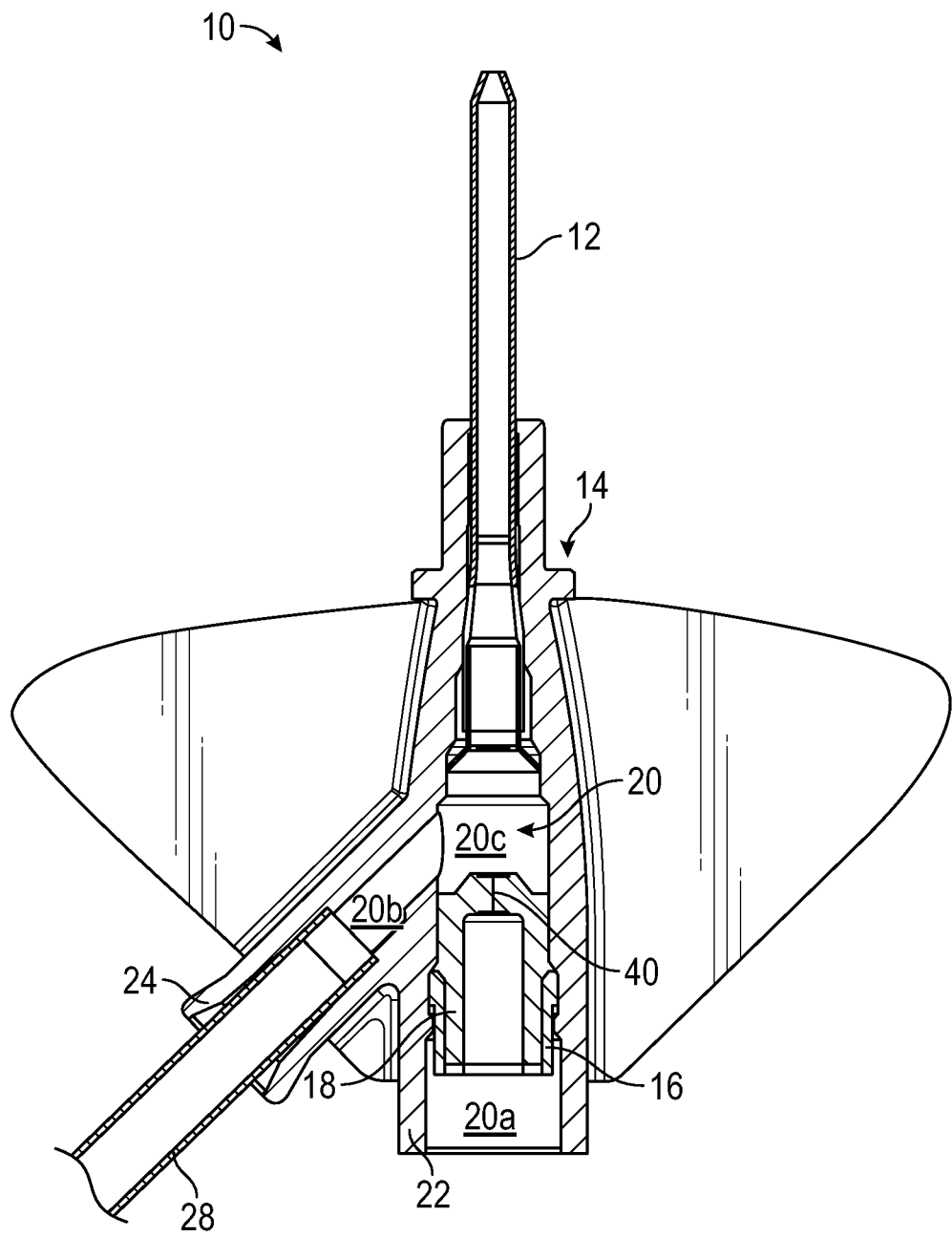
FIG. 1A is a cross-sectional top view of an example catheter assembly, according to some embodiments.
Figure 1B:
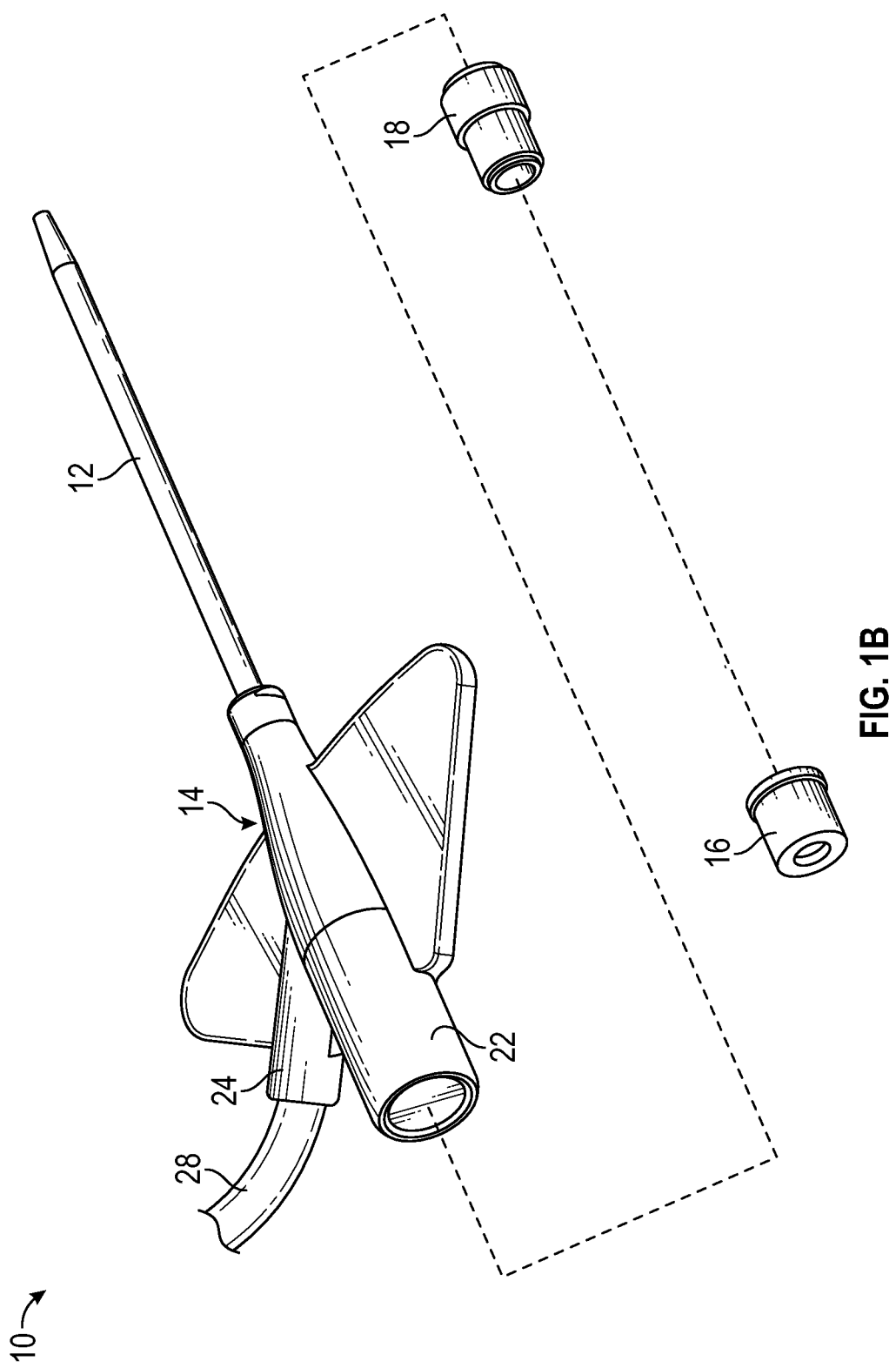
FIG. 1B is a partial exploded view of the catheter assembly of FIG. 1A, according to some embodiments.
Figure 1C:
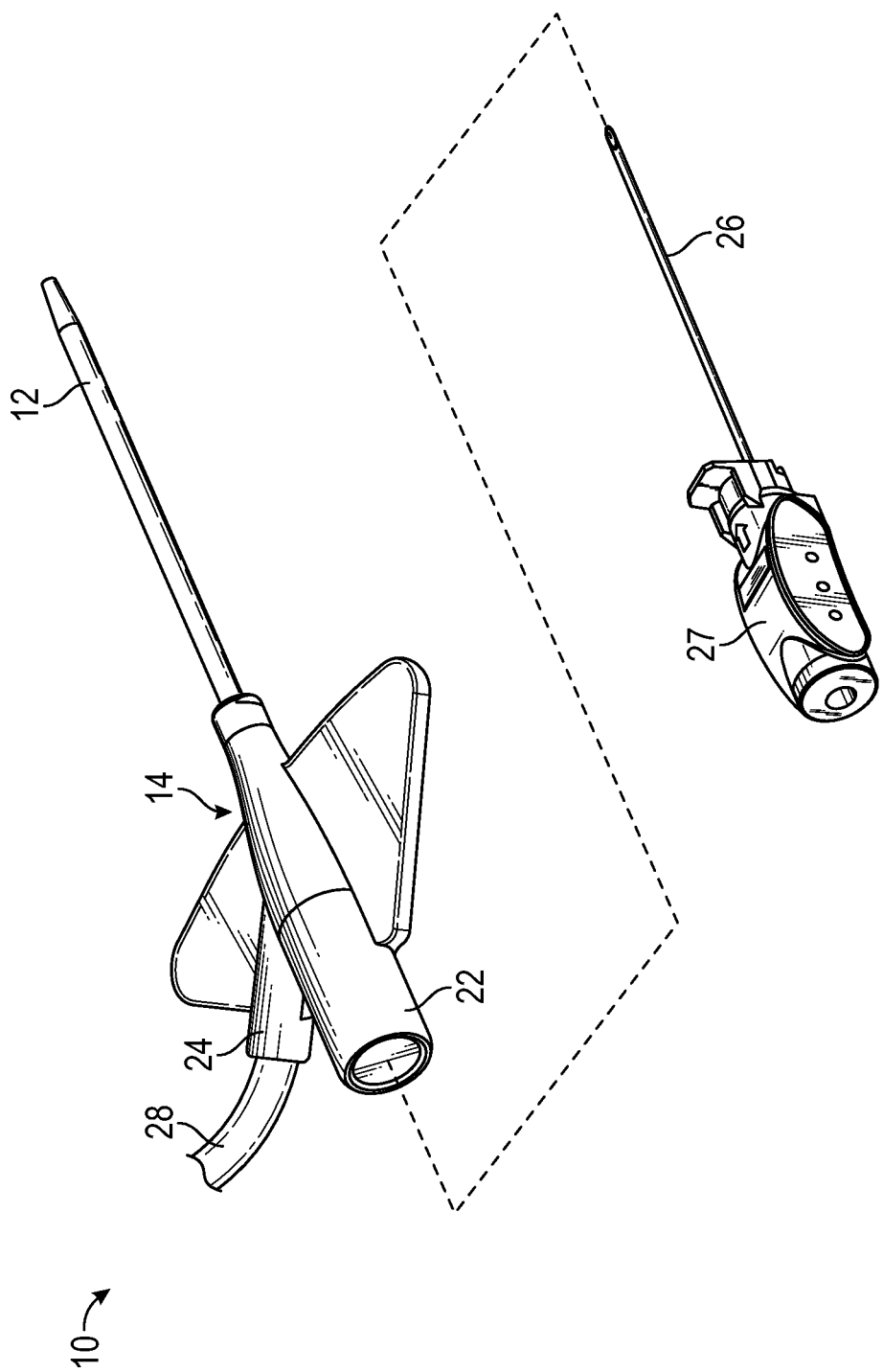
FIG. 1C is an upper perspective view of an example needle hub configured to be coupled with the catheter assembly of FIG. 1A, according to some embodiments.

The present application relates generally to instrument guidance within a catheter system, which may include a peripheral IV catheter system. Referring now to FIGS. 1A-1C, in some embodiments, the catheter system may include a catheter assembly 10. In some embodiments, the catheter assembly may include one or more of the following: a catheter 12, a catheter adapter 14, a septum housing 16, and a septum 18.

In some embodiments, the catheter adapter 14 may include a distal end, a proximal end, and a lumen 20 extending therebetween. In some embodiments, the septum 18 may be disposed within the lumen 20 of the catheter adapter 14. In some embodiments, the septum 18 may be at least partially disposed within the septum housing 16. In some embodiments, the septum housing 16 may prevent dislodgement or destabilization of the septum 18, thereby preventing leakage of fluid from the catheter adapter 14. In some embodiments, the septum 18 and the septum housing 16 may include or correspond to any of the septa 18 and septum housings 16, respectively, illustrated in any of the other Figures.

In some embodiments, the catheter assembly 10 may be part of a closed IV catheter system or catheter system with an integrated extension tube, such as, for example, the BD NEXIVA™ Closed IV Catheter System, the BD NEXIVA™ DIFFUSICS™ Closed IV Catheter System, or the Becton Dickinson PEGASUS™ Safety Closed IV Catheter System.

In these and other embodiments, a proximal end of the catheter adapter 14 may include a first port 22 and a second port 24. In these and other embodiments, the lumen 20 of the catheter adapter 14 may include a first lumen 20a and/or a second lumen 20b. In some embodiments, the first port 22 may form the first lumen 20a and/or the second port 24 may form the second lumen 20b. In some embodiments, the first and second lumens 20a,20b may join at a common lumen 20c. In some embodiments, the first lumen 20a may be generally aligned with the common lumen 20c and/or the second port 24 may include a side port. In some embodiments, the septum 18 and/or the septum housing 16 may be disposed in the first lumen 20a. In some embodiments, the septum 18 may be configured to at least substantially seal the first lumen 20a of the catheter adapter 14.

In the integrated or closed IV catheter system, an introducer needle 26 may be withdrawn through the catheter adapter 14 after insertion of the catheter 12 into the vasculature of a patient. In the integrated or closed IV catheter system, when the introducer needle 26 is withdrawn through the catheter adapter 14, the first lumen 20a, which may correspond to a "needle channel," may be closed off by the septum 18 from an external environment surrounding the catheter adapter 14. Thus, the septum 18 may prevent fluid from exiting the catheter adapter 14 through the first port 20a. In some embodiments, a fluid pathway of the catheter assembly 10 during fluid infusion and/or blood withdrawal may extend through the second port 20b and may not extend through the first port 20a and the septum 18.

In some embodiments, the second lumen 20b of the catheter adapter 14 may be connectable to blood withdrawal or infusion means via an extension tube 28 that may extend from the second port 20b of the catheter adapter 14. In some embodiments, the septum 18 and/or the septum housing 16 may be disposed proximal to the second port 20b of the catheter adapter 14.

It is understood that the catheter assembly 10 may include any number of ports. For example, the catheter assembly 10 may include a single port in which the septum 18 and/or the septum housing 16 may be disposed. In some embodiments, the catheter assembly 10 may include the first port 20a, the second port 20b, and one or more additional ports. In some embodiments, fluid may be prevented by the septum 18 from exiting the catheter adapter 14 via a particular port in which the septum 18 is disposed. In some embodiments, the catheter assembly 10 may be part of another type of catheter system, such as, for example, a non-integrated catheter system. In some embodiments, the extension tubing 28 and/or second port 20b may be absent. In these and other embodiments, the fluid pathway of the catheter adapter 14 may extend through the septum 18.

In some embodiments, the septum 18 may include a slit 40. In further detail, in some embodiments the septum 18, may be pre-slit prior to insertion of the introducer needle 26 through the septum 18 or the slit 40 may be formed when the introducer needle 26 is inserted through the septum 18. In some embodiments, the introducer needle 26 may be coupled to a needle hub 27, which may include a needle safety mechanism.

Figure 2A:
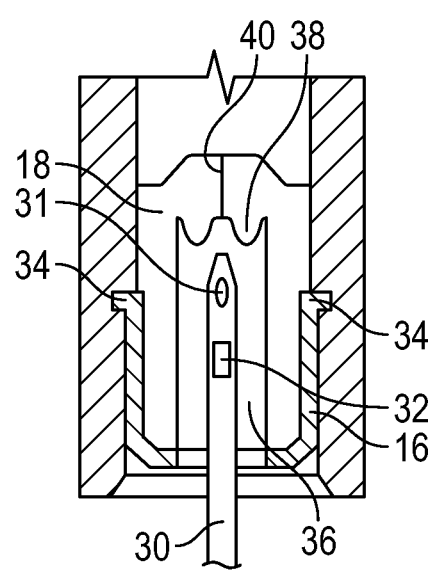
FIG. 2A is a cross-sectional view of an example septum that includes a guidance feature, according to some embodiments.
Figure 2B:
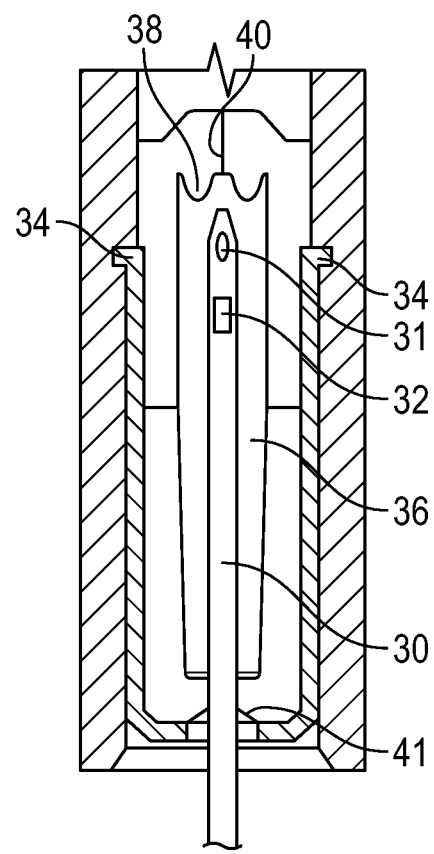
FIG. 2B is a cross-sectional view of another example septum that includes the guidance feature of FIG. 2A and another guidance feature, according to some embodiments.
Figure 2C:
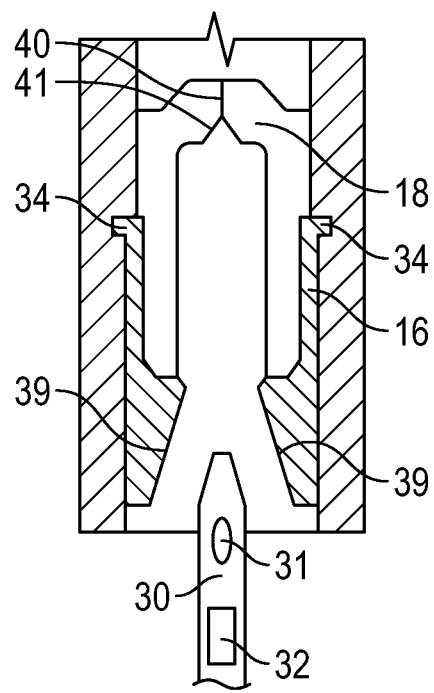
FIG. 2C is a cross-sectional view of a septum housing having another example guidance feature, according to some embodiments, according to some embodiments.
Figure 3A:
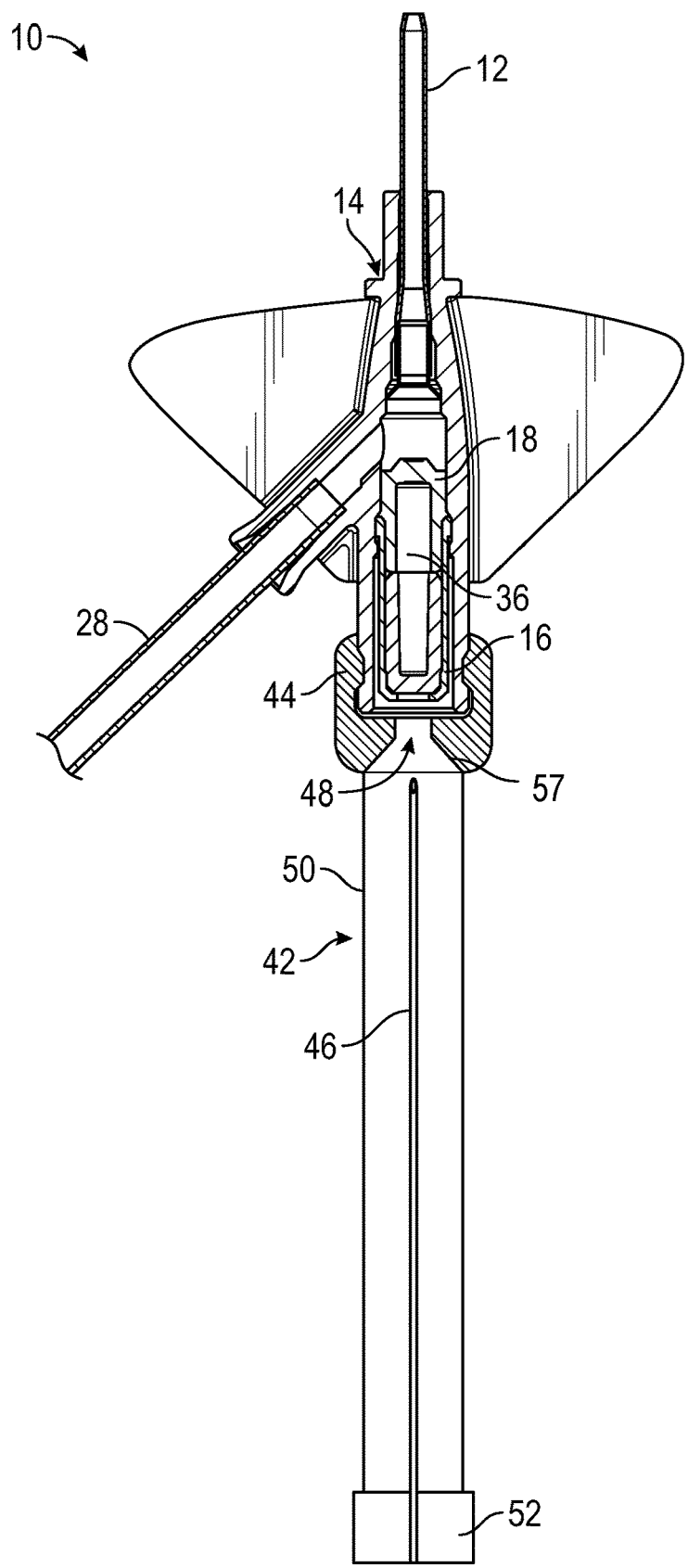
FIG. 3A is a cross-sectional view of an example introducer coupled to another example catheter assembly, illustrating the introducer in a first position, according to some embodiments.
Figure 3B:
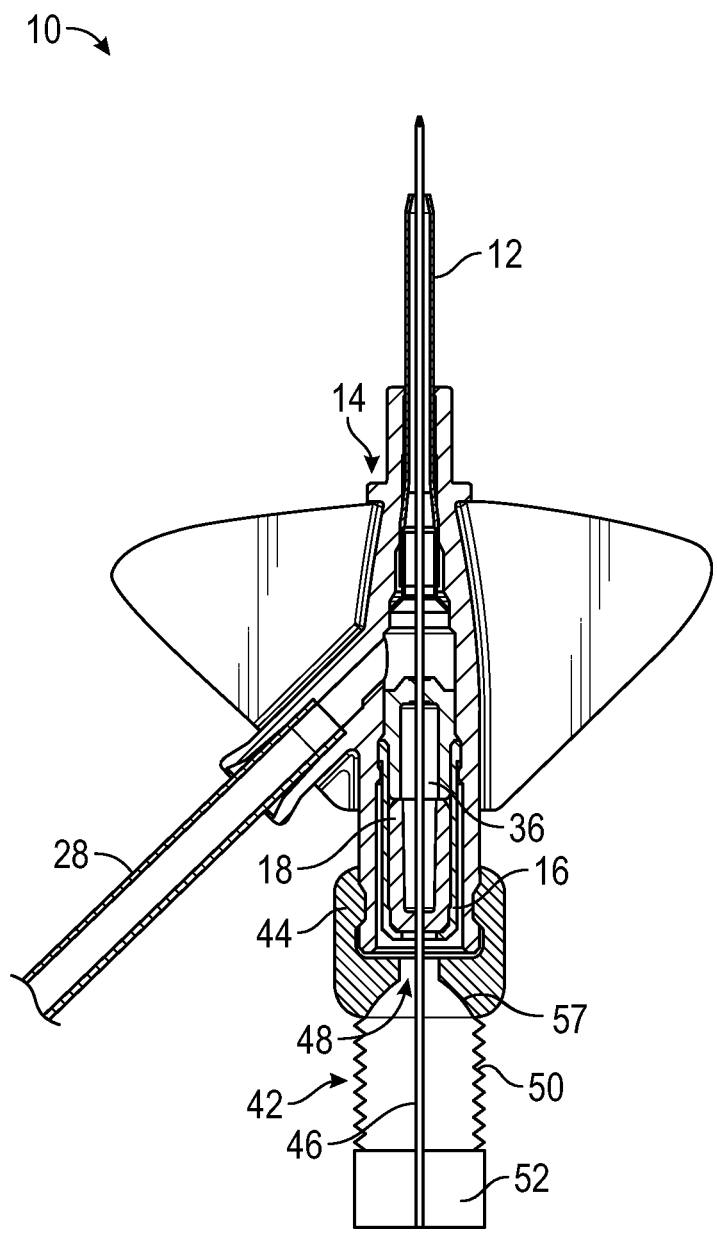
FIG. 3B is a cross-sectional view of the introducer of FIG. 3A, illustrating the introducer in a second position, according to some embodiments.

Referring now to FIGS. 2A-2C, in some embodiments, an instrument may include another catheter and/or a probe 30. An example of the probe 30 is illustrated in FIGS. 2A-2C. However, the probe 30 may be replaced with the other catheter, an example of which is illustrated in FIGS. 3A-3B. In some embodiments, the instrument may function as both the probe 30 and the other catheter. In some embodiments, the instrument may be useful for one or more of the following: diagnostics, blood sampling, monitoring, and one or more other purposes.

In some embodiments, the instrument may be guided by one or more features of the catheter system, such as, for example, one or more tapered surfaces, to allow the instrument to access the fluid pathway of the catheter assembly 10 and/or the vasculature of the patient. In some embodiments, the one or more features of the catheter system may include lead-in features and/or may guide the instrument through the septum 18 to access the fluid pathway of the catheter assembly 10. In some embodiments, by accessing the fluid pathway and/or the vasculature through the septum 18, insertion of the instrument through a long and tortuous path of an integrated extension set may be avoided.

In some embodiments, the other catheter may include a replacement catheter, which may be needleless. In some embodiments, the probe 30 may include one or more openings 31 and/or one or more sensors 32. In some embodiments, the openings 31 and/or the sensors 32 may be disposed towards a distal tip of the probe 30. In some embodiments, the openings 31 may serve as fluid inlets and/or outlets. In some embodiments, the sensors 32 may measure one or more parameters and/or detect one or more elements related to, for example, diagnostic information, blood chemistry, pressure, flow rate, drug identification, microbes, placement of an implantable stent, in-vein catheter tip stabilization feature, or other device, etc. In some embodiments, the one or more features may facilitate placement of a portion of the probe 30 that includes the sensors 32 within the fluid pathway of the catheter assembly 10 and/or the vasculature of the patient.

In some embodiments, the septum 18 may be a low-drag septum designed to reduce friction on the instrument passing through the septum 18, which may aid in threading the instrument through the septum 18. In some embodiments, the septum 18 may be configured to withstand high pressures within the catheter assembly 10. In some embodiments, the septum housing 16 and/or the septum 18 may be secured within the catheter adapter 14 in any number of ways. In some embodiments, the septum housing 16 may include one or more protrusions 34. In some embodiments, the one or more protrusions 34 may include a lip. In some embodiments, the septum housing 16 may be secured to an inner wall of the catheter adapter 14 by one or more of the following: an interference fit between the one or more protrusions 34 and the inner wall, a snap fit between the one or more protrusions 34 and the inner wall, bonding between the one or more protrusions 34 and the inner wall, and threading securing the one or more protrusions 34 to the inner wall. In some embodiments, the inner wall may include a groove or opening.

In some embodiments, the septum housing 16 may be resilient, and in response to the one or more protrusions 34 aligning with the groove or opening, the septum housing 16 may resiliently move outward to retain the one or more protrusions 34 within the groove or opening in the snap fit. In further detail, in some embodiments, in response to the septum housing 16 being inserted into the proximal end of the catheter adapter 14, the one or more protrusions 34 may be biased inwardly and/or in response to the one or more protrusions being further inserted into the proximal end and aligning with the groove or opening, the one or more protrusions 34 may move resiliently outward such that the one or more protrusions 34 are retained in the groove or opening.

In some embodiments, the bonding between the septum housing 16 and the inner wall and/or between the septum 18 and the inner wall may be disposed at various locations on the inner wall. In some embodiments, one or more of the following: adhesive bonding, chemical bonding, ultrasonic welding, and laser welding, may be disposed on all or some surfaces of the inner wall and/or the septum 18 that are in contact. Additionally or alternatively, one or more of the following: adhesive bonding, chemical bonding, ultrasonic welding, and laser welding, may be disposed on all or some surfaces of the inner wall and/or the septum housing 16 that are in contact.

In some embodiments, the septum 18 and/or the septum housing 16 may be retained within the catheter adapter 14 without requiring a mechanical or interference interface with the septum housing 16. For example, the proximal end of the catheter adapter 14 may abut and extend over a portion of a surface area of a proximal face of the septum 18 and/or the septum housing 16, thereby retaining the septum 18 and/or the septum housing 16 within the catheter adapter 14. Thus, the catheter adapter 14 may prevent the septum 18 and/or septum housing 16 from moving proximally within the catheter adapter 14 due to a wall at the proximal end of the catheter adapter 14 that abuts and thereby partially blocks the proximal end of the catheter adapter 14.

Referring now to FIGS. 2A-2B, in some embodiments, the septum 18 may include one or more guiding features that may facilitate guidance of the instrument distally through the septum 18. As an example, in some embodiments, the septum 18 may include an proximal surface that is tapered inwardly in a distal direction such that the proximal surface of the septum 18 is configured to guide the instrument distally through the septum 18. In some embodiments, the proximal surface of the septum 18 may be funnel-shaped or conical-shaped. In some embodiments, the septum 18 may include a cavity 36. In some embodiments, a distal end of the cavity 36 may include the proximal surface of the septum 18. In some embodiments, a slit 40 of the septum 18 may be disposed at or near a center of the proximal surface. In some embodiments, the distal end of the cavity 36 may include an annular protrusion 38, which may form the proximal surface of the septum 18. In some embodiments, the slit 40 may be disposed at or near a center of the annular protrusion 38. In some embodiments, the one or more guiding features of the septum 18 may include ribs, protrusions, grooves, or other guiding features that may facilitate direction of the instrument. In some embodiments, the proximal surface of the septum 18 may include the one or more guiding features. In some embodiments, guiding the instrument may include contacting the one or more guiding features.

In some embodiments, the one or more guiding features of the septum 18 may be disposed at a proximal end of the septum 18. For example, the proximal surface of the septum 18 may be disposed at a proximal end of the septum 18. FIG. 2B illustrates the proximal surface disposed at the proximal end of the septum and the proximal surface as a funnel-shape 41, for example.

Figure 2D:
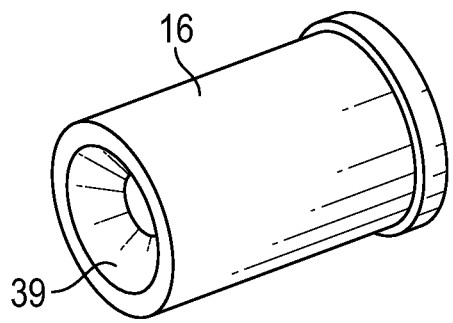
FIG. 2D is an upper perspective view of the septum housing of FIG. 2C, according to some embodiments.

Referring now to FIGS. 2C-2D, in some embodiments, the septum housing 16 may include one or more guiding features that may facilitate guidance of the instrument distally through the septum 18 and/or the septum housing 16. As an example, in some embodiments, the septum housing 16 may include a proximal surface 39 that is tapered inwardly in the distal direction such that the proximal surface 39 is configured to guide the instrument distally through the septum 18. In some embodiments, the proximal surface 39 may be funnel-shaped or conical-shaped. In some embodiments, the septum housing 16 may include a distal end and a proximal end. In some embodiments, the septum 18 may be at least partially disposed within the distal end of the septum housing 16. In some embodiments, the proximal end of the septum housing 16 may include the proximal surface 39. In some embodiments, the septum housing 16 may include a canister, as illustrated, for example, in FIG. 2D.

In some embodiments, the one or more guiding features of the septum housing 16 may include ribs, protrusions, grooves, or other guiding features that may facilitate direction of the instrument. In some embodiments, the proximal surface of the septum housing 16 may include the guiding features. The proximal surface of the septum 18 illustrated in FIG. 2C illustrates the funnel-shape 41, as an example proximal surface. In some embodiments, a particular port of the catheter adapter 14 may include the one or more guiding features of the septum housing 16 and/or the septum housing 16 may be integrally formed with the particular port of the catheter adapter 14.

Referring now to FIGS. 3A-3B, in some embodiments, the catheter system may include an introducer 42, which may be configured to introduce the instrument into the catheter assembly 10. In some embodiments, the instrument may include another catheter 46, as illustrated, for example, in FIGS. 3A-3B. However, the catheter 46 may be replaced with the probe 30, an example of which is illustrated in FIGS. 2A-2C. In some embodiments, the instrument may function as both the probe 30 and the other catheter 46, including elements of both the probe 30 and the other catheter 46.

In some embodiments, the introducer 42 may include an introducer element 44, which may be coupled with the proximal end of the catheter adapter 14. In some embodiments, the introducer element 44 may include one or more guiding features that may facilitate guidance of the instrument distally through the septum. As an example, in some embodiments, a proximal end of the introducer element 44 may include an opening 48 at least partially formed by a proximal and/or inner surface 57, which may be tapered inwardly in the distal direction such that the inner surface 57 is configured to guide the instrument distally through the introducer element 44 and through the slit 40 of the septum 18. In some embodiments, the inner surface 57 may be conical-shaped or funnel-shaped, as illustrated, for example, in FIG. 3A. In some embodiments, the inner surface 57 may include one or more ribs, protrusions, grooves, or other guiding features that may facilitate direction of the instrument.

In some embodiments, the introducer element 44 may include one or more coupling mechanisms that may facilitate coupling between the proximal end of the catheter adapter 14 and the introducer element 44, which may prevent fluid leakage and/or contamination of the fluid pathway when the instrument is inserted within the catheter assembly 14. In further detail, in some embodiments, the introducer element 44 may be coupled with the proximal end of the catheter adapter 14 in any number of ways, such as, for example, snap-fit, threads, press-fit, interference-fit, or another suitable means. In some embodiments, a particular coupling mechanism of the introducer element 44 may be coupled to a particular port of the catheter adapter. As illustrated in FIGS. 3A-3B, in some embodiments, one or more protrusions may snap into one or more recesses of the catheter adapter 14.

In some embodiments, the catheter adapter 14 and/or the introducer element 44 may be monolithically formed as a single piece. In some embodiments, the instrument may be coupled with the introducer element 44. In other embodiments, the instrument may not be coupled with the introducer element 44.

In some embodiments, the introducer 42 may include a sheath or sleeve 50, which may be coupled to the introducer element 44. In some embodiments, the sleeve 50 may surround the instrument. In these and other embodiments, the sleeve 50 may shield the instrument from contaminants and/or isolate any blood or other fluids that may remain on the instrument after accessing the fluid pathway of the catheter assembly 10. In these and other embodiments, the sleeve 50 may protect the instrument from the external environment surrounding the introducer 42.

In some embodiments, the instrument may be at least partially disposed within the sleeve 50. In some embodiments, the sleeve 50 may constructed of a flexible and/or compliant material. In some embodiments, the sleeve 50 may be axially-collapsible or axially-compressible. In further detail, in some embodiments, the instrument may be advanced to a position beyond a distal end of the sleeve 50 when the sleeve is collapsed or compressed in the distal direction. In some embodiments, the introducer 42 may include a handle or grip 52, which may be coupled to a proximal end of the sleeve 50. In some embodiments, the clinician may move the grip 52 distally to collapse or compress the sleeve 50 in the distal direction and advance the instrument to the position beyond the distal end of the sleeve 50.

In some embodiments, various types of sleeves 50 may be used. In some embodiments, the introducer 42 may include a housing (not illustrated), which may be coupled with the introducer element 44. In some embodiments, the housing may include one or more components, such as, for example, concentric barrels. In some embodiments, at least a portion of the housing may be axially-collapsible or axially-compressible. For example, a first concentric barrel may be advanced into a second concentric barrel.

In some embodiments, the sleeve 50 may be at least partially disposed within the housing, which may be rigid or semi-rigid. An example housing is described in U.S. Provisional Patent Application. No. 62/534,552, filed Jul. 19, 2017, entitled "Extension Housing a Probe or Intravenous Catheter," which is hereby incorporated by reference in its entirety. In some embodiments, the housing may include a slot. In some embodiments, a tab or an adapter may be coupled with the proximal end of the instrument or near the proximal end of the instrument. In some embodiments, the tab or the adapter may be configured to move along the slot from a proximal position to a distal position. In some embodiments, in response to movement of the adapter from the proximal position to the distal position, the instrument may be advanced beyond the distal end of the sleeve 50 and/or the housing. In some embodiments, the adapter may include a cavity configured to receive a syringe or blood collection tube and/or a cannula configured to puncture a septum of the syringe and/or the blood collection tube. An example slot and example adapter is described in U.S. Provisional Patent Application. No. 62/534,552, filed Jul. 19, 2017, entitled "Extension Housing a Probe or Intravenous Catheter."

As mentioned, in some embodiments, at least a portion of the housing may be axially-collapsible or axially-compressible. For example, the housing may include one or more collapsing and/or telescoping barrels. Additionally or alternatively, the housing may include the slot. In some embodiments, a first concentric barrel may be advanced into a second concentric barrel. In some embodiments, at least a portion of the first concentric barrel and/or the second concentric barrel may be collapsible.

In some embodiments, the introducer 42 may not include the sleeve 50 and/or the grip 52. In these and other embodiments, the introducer element 44 may have an extended length such that a portion of the introducer element 44 protrudes from underneath a dressing used to cover an insertion site of the catheter 12, facilitating easy access to the septum 18 and/or supporting the instrument.

In some embodiments, the introducer element 44, the grip 52, or another portion of the introducer 42 may be connected to a luer fitting, Becton Dickinson LUER-LOK™ Access Device, or another device for blood collection and/or monitoring. In some embodiments, a fluid pathway of the introducer 42 may extend through the grip 52. In some embodiments, the introducer element 44, the grip 52, or another portion of the introducer 42 may be connected to a monitoring interface and/or monitoring equipment.

Figure 3C:
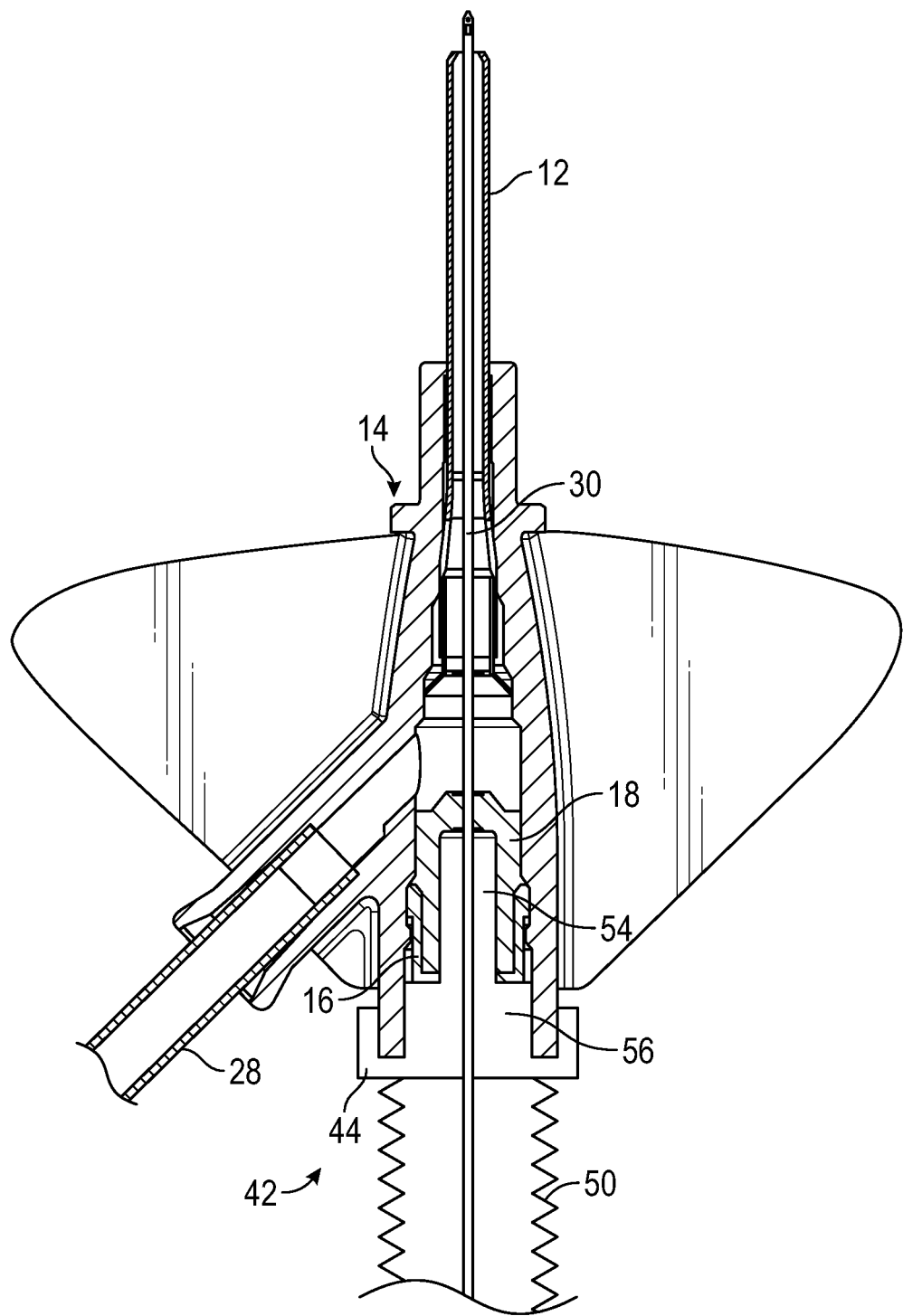
FIG. 3C is a cross-sectional view of another example introducer, illustrating the introducer in the second position, according to some embodiments.

Referring now to FIG. 3C, in some embodiments, the introducer element 44 may include a coupling mechanism. In some embodiments, a proximal end of the introducer element 44 may include the coupling mechanism. In some embodiments, a distal end of the introducer element may include a tube 54. In some embodiments, the coupling mechanism may be disposed proximal to the tube 54. In some embodiments, in response to the introducer 42 being coupled to the catheter adapter 14 via the coupling mechanism of the introducer element 44, the tube 54 may be disposed within the cavity 36 and/or proximate a proximal face of the septum 18. In these and other embodiments, the tube 54 may not penetrate the septum 18. In these and other embodiments, the tube 54 may contact the proximal face of the septum 18 proximate the slit 40. In some embodiments, the proximal face may be disposed within the cavity 36, although in some embodiments, the septum 18 may not include the cavity 36 and/or first and second proximally-extending arms forming the cavity 36. In some embodiments, a width of the tube 54 may be approximately equal to a width of the cavity 36. In some embodiments, a distal end of the tube 54 may be blunt, which may prevent harm to the septum 18. In some embodiments, the tube 54 may extend from a base 56 portion of the introducer element 44. FIG. 3C illustrates the probe 30, which may be replaced with the other catheter 46, as previously mentioned.

Figure 3D:
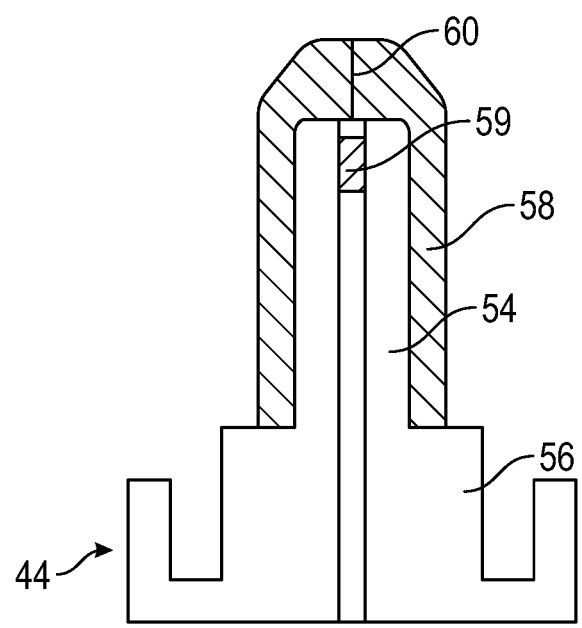
FIG. 3D is a cross-sectional view of an example cover disposed on an example introducer element, according to some embodiments.

Referring now to FIG. 3D, in some embodiments, the introducer element 44 may include a fluid seal, which may prevent fluid from entering a distal opening of the tube 54. For example, the introducer element 44 may include a cover 58, which may be configured to be penetrated by the instrument and provide a seal between the septum 18 and the introducer element 44. In some embodiments, the cover 58 disposed over top or at least partially covering the tube 54. In some embodiments, the cover 58 may cover the distal opening of the tube 54. In some embodiments, the cover 58 may be elastomeric and compliant. In some embodiments, the cover 58 may include a slit 60, which may facilitate penetration of the cover 58 by the instrument. In some embodiments, the cover 58 may include one or more antimicrobial agents. In some embodiments, the cover 58 may facilitate a fluid seal against the proximal face of the septum 18.

In some embodiments, the introducer 42 may include at least one valve 59, which may provide a seal that is penetrated by the instrument. In some embodiments, the valve 59 may include a slit. The valve 59 of the introducer 42 may be disposed at any number of locations to prevent fluid from the catheter assembly 10 from entering all or a portion of the introducer 42 and/or exiting the proximal end of the introducer. An example valve 59 is illustrated in FIG. 3D. In some embodiments, the introducer 42 may include the valve 59 and/or the cover 58. In some embodiments, when the introducer 42 does not penetrate the septum 18, such as, for example, in FIG. 3C, the introducer 42 may not include the valve 59 and/or the cover 58.

In some embodiments, any of the components of the catheter system, including any component of the introducer 42 and/or any component of the catheter assembly 10, for example, may include one or more antimicrobial agents, such as for example, an antimicrobial coating antimicrobial lubricant, etc. In some embodiments, the antimicrobial agents may reduce a risk of contamination of a fluid pathway of the catheter system.

Figure 4A:
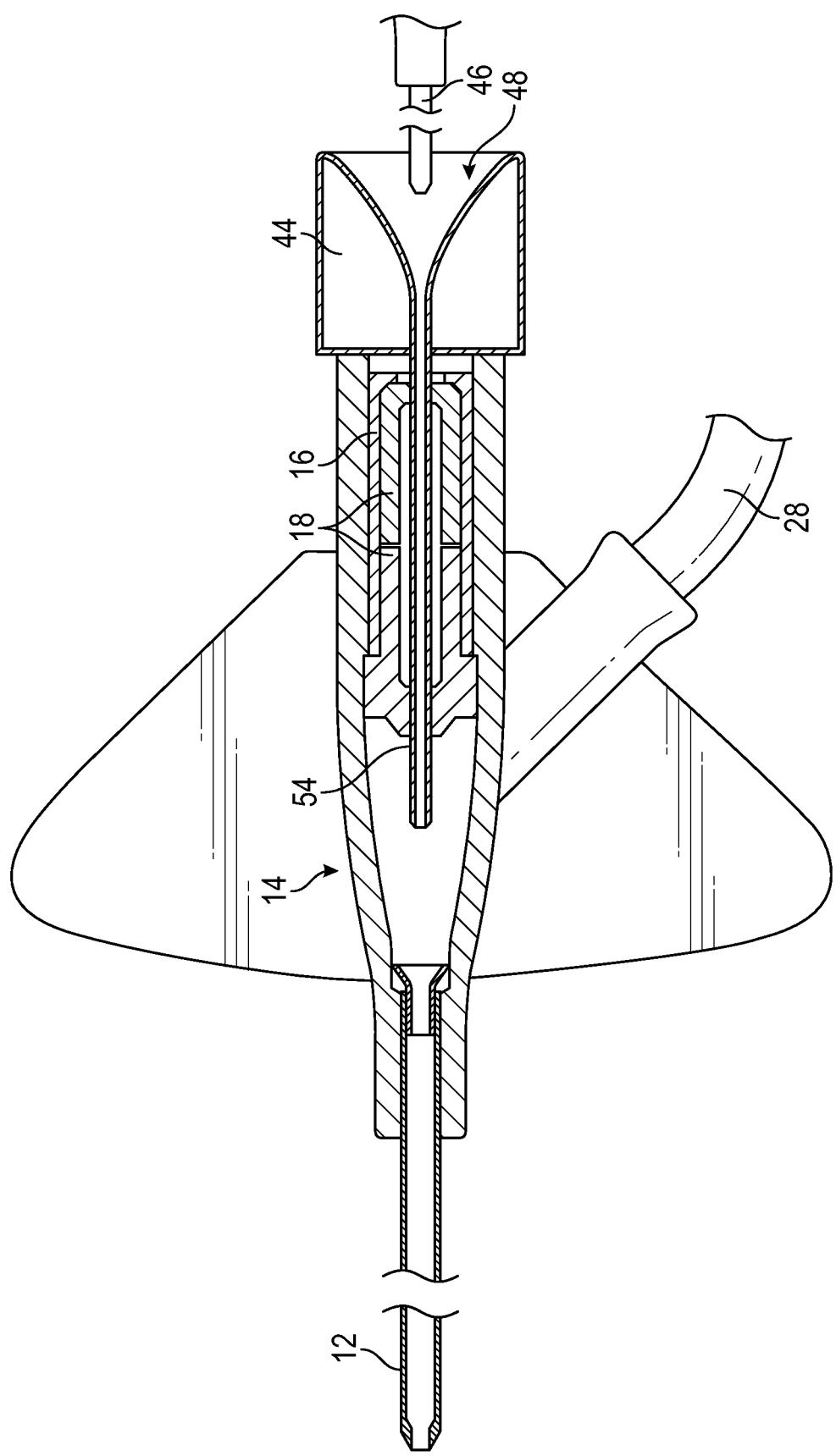
FIG. 4A is a cross-sectional view of another example introducer, according to some embodiments.
Figure 4B:
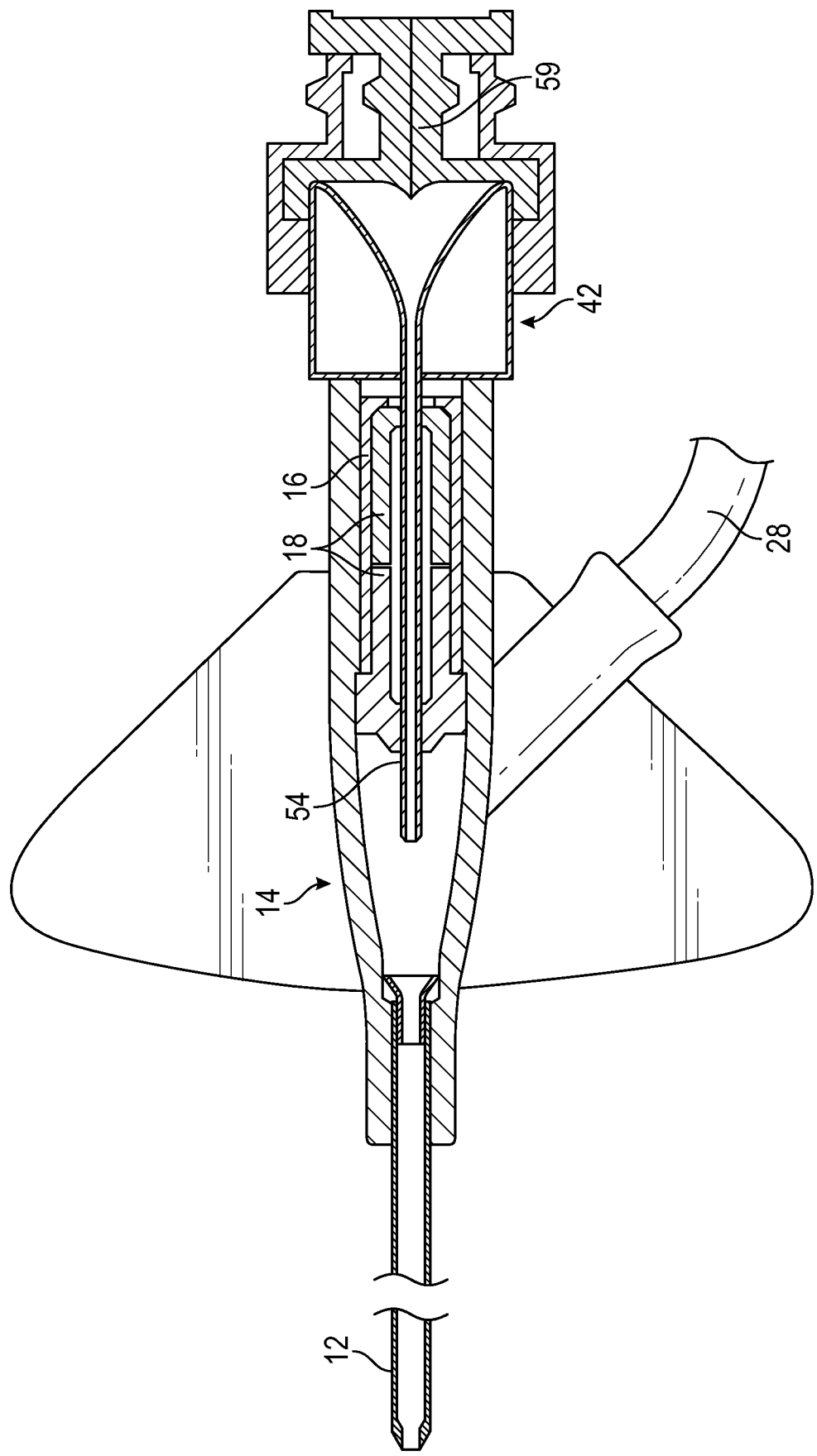
FIG. 4B is a cross-sectional view of the introducer of FIG. 4A, according to some embodiments.

Referring now to FIGS. 4A-4B, in some embodiments, in response to the introducer 42 being coupled to the catheter adapter 14 via the coupling mechanism of the introducer element 44, the tube 54 may penetrate the septum 18. In these and other embodiments, fluid within the cavity 36 of the septum 18 may be reduced and/or a compressive axial load on the instrument may be decreased compared to when the instrument itself opens the septum 18. In some embodiments, a distal end of the tube 54 may be blunt, which may prevent harm to the septum 18. In some embodiments, the introducer 42 of FIGS. 4A-4B may include one or more of the sleeve 50, the grip 52, and one or more other components discussed with respect to FIGS. 1-3. FIG. 4 illustrates the catheter 46 prior to insertion within the introducer 44, according to some embodiments.

Another example valve 59 is illustrated in FIG. 4B. In some embodiments, the valve 59 may be disposed within a needleless connector. In some embodiments, the needleless connector may form a proximal end of the introducer element 44. In some embodiments, the valve 59 may be disposed within the catheter adapter 14 distal to the septum 18. In these embodiments, the tube 54 may penetrate the septum 18 but not the valve 59, which may be penetrated by the instrument. In some embodiments, the valve 59 may provide less resistance to the instrument than the septum 18.

Figure 5:
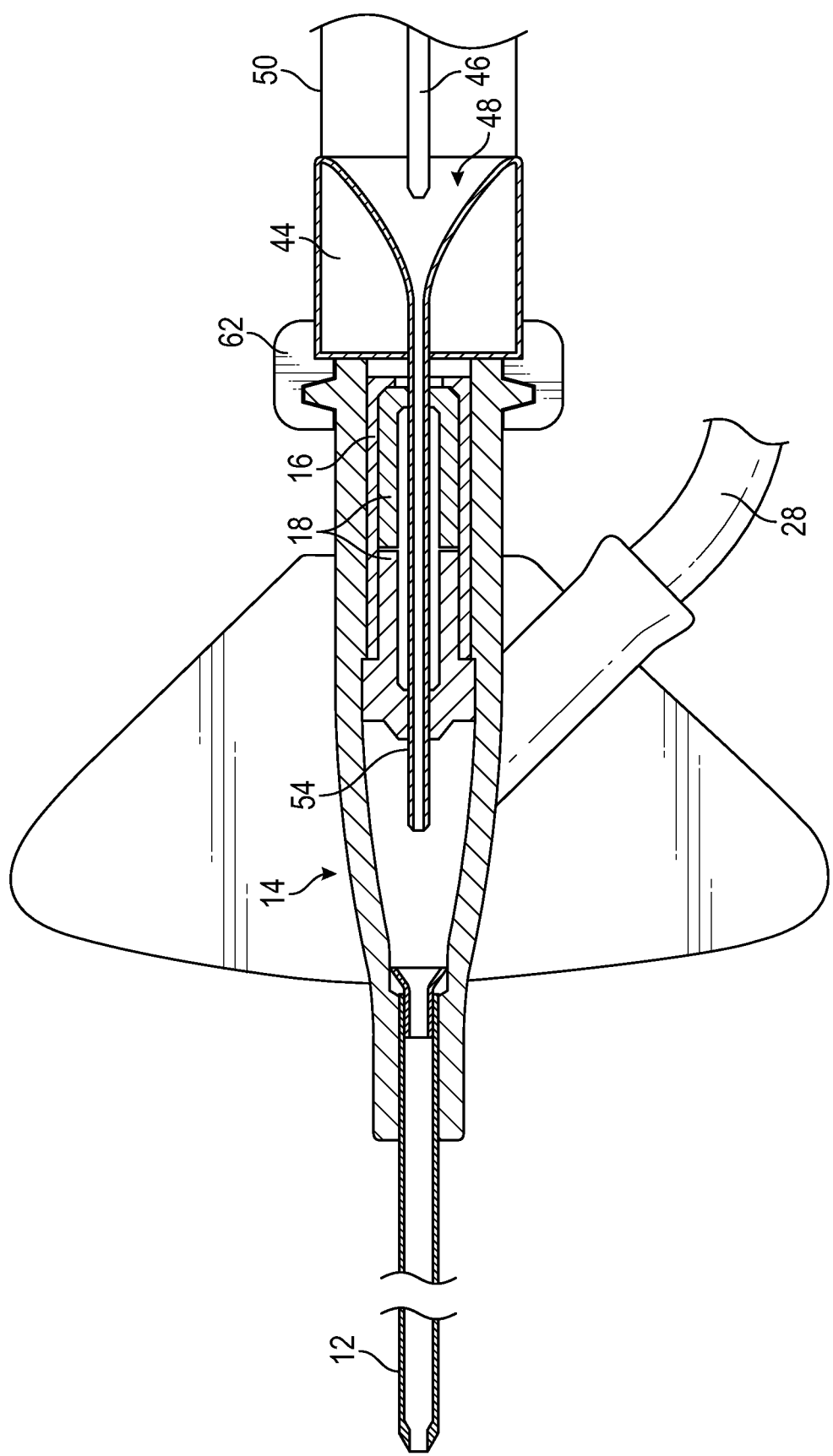
FIG. 5 is a cross-sectional view of the introducer of FIG. 4A, according to some embodiments.
Figure 6A:
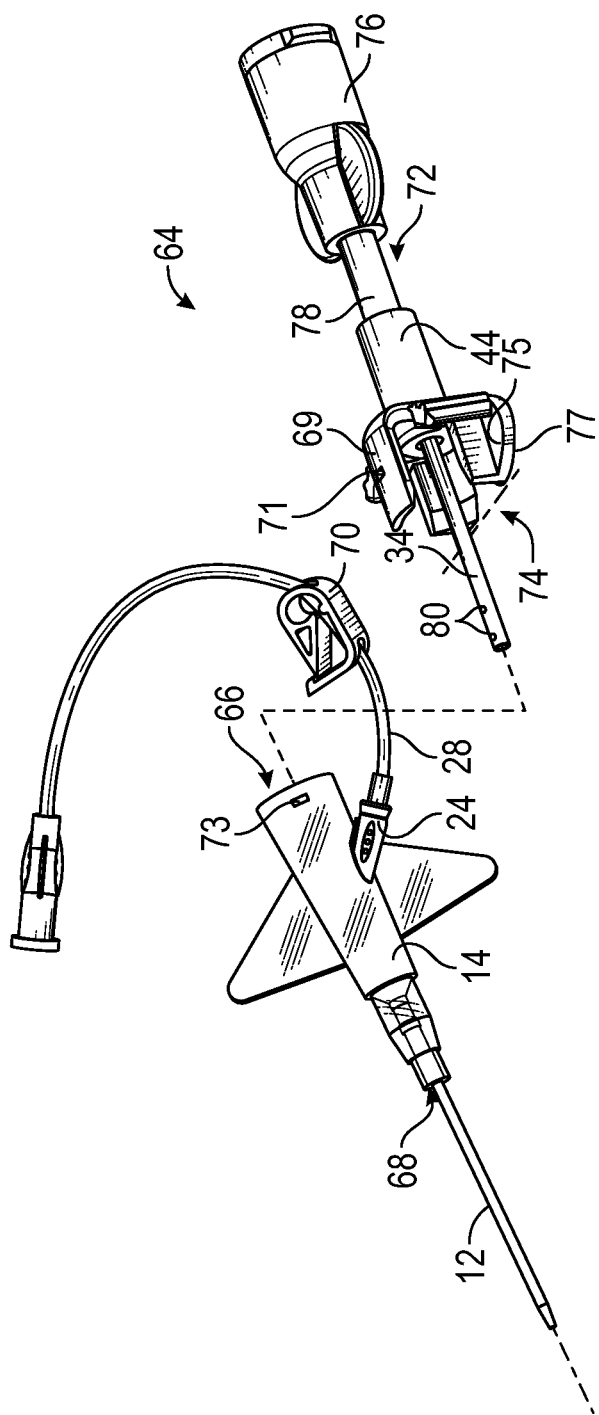
FIG. 6A is an exploded view of an example system having an example catheter assembly and example extension set, according to some embodiments.
Figure 6B:
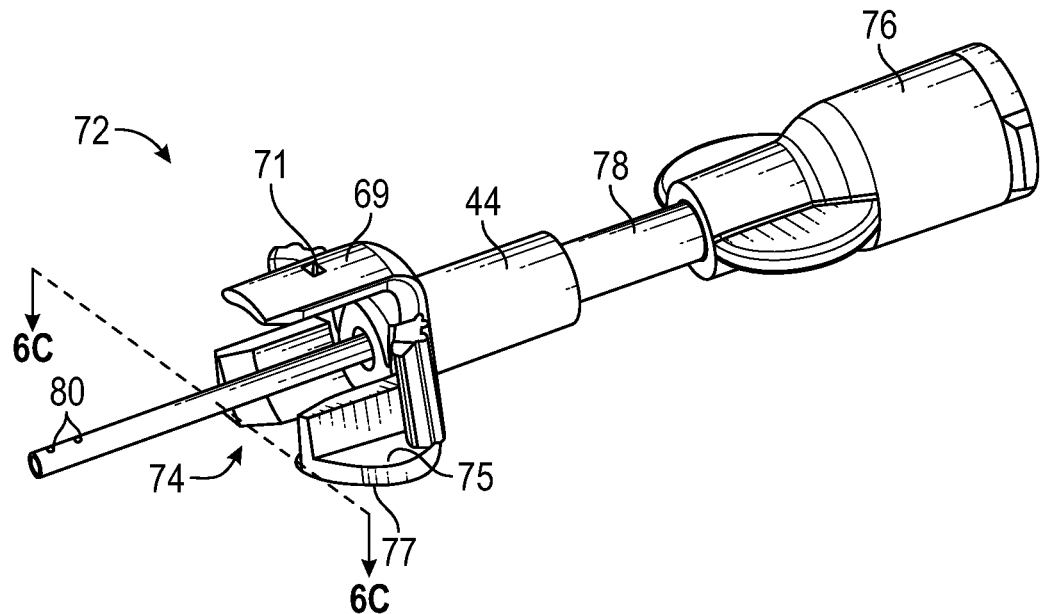
FIG. 6B is an upper perspective view of the extension set of FIG. 6A, according to some embodiments.
Figure 6C:
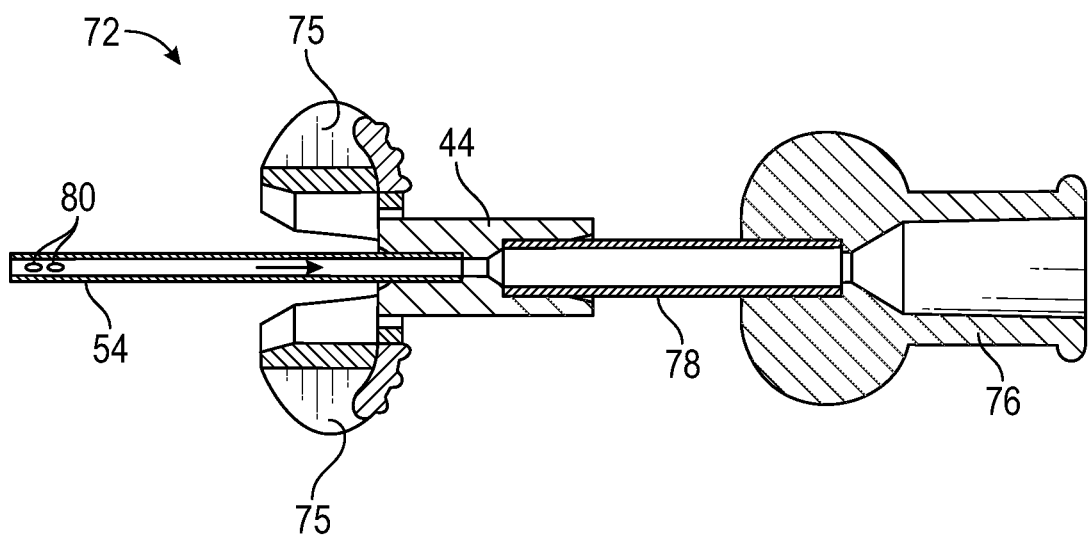
FIG. 6C is a cross-sectional view of the extension set of FIG. 6B along the line 6C-6C, according to some embodiments.
Figure 6D:
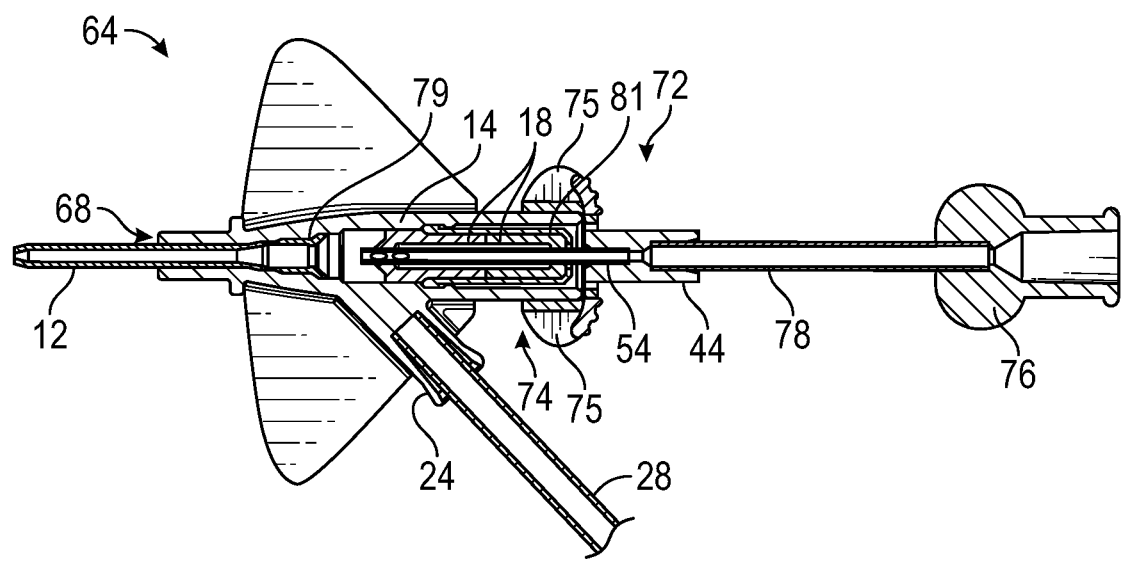
FIG. 6D is a cross-sectional view of the system of FIG. 6A, according to some embodiments.

Referring now to FIG. 5, as explained previously, in some embodiments, the introducer element 44 may be coupled with the proximal end of the catheter adapter 14 via any number of coupling mechanisms. For example, the introducer element 44 may be coupled with the proximal end of the catheter adapter via a snap-fit, threads, a press-fit, an interference-fit, etc. In some embodiments, the introducer 44 may include a connector 62, which may include the one or more coupling mechanisms, such as, for example, threads, as illustrated in FIG. 5. In some embodiments, the connector 62 may be coupled to the proximal end of catheter adapter 14 via the one or more coupling mechanisms. In some embodiments, the connector 62 may be removable from the introducer element 44 and/or the catheter adapter 14. In other embodiments, the connector 62 may be non-removable from or permanently coupled to the introducer element 44 and/or the catheter adapter 14. FIG. 5 illustrates the introducer element 44 coupled with the sleeve 50, according to some embodiments.

In some embodiments, the present disclosure relates generally to devices, systems, and methods for facilitating delivery of an instrument through a peripheral intravenous catheter ("PIVC"). In some embodiments, the instrument may include an additional catheter for fluid infusion or blood draw, a guidewire, a probe with a sensor, or a light tube for disinfection.

Referring now to FIGS. 6A-6D, in some embodiments, a system 64 for facilitating instrument delivery through the catheter 12 may include the catheter adapter 14, the catheter 12 extending distally from the catheter adapter 14, and the extension tube 28 extending from the second or side port 24 of the catheter adapter 14. In some embodiments, the catheter adapter 14 may include a proximal end 66 and a distal end 68.

In some embodiments, the system 64 may include a Y-adapter or another adapter, which may be coupled to a proximal end of the extension tube 28. In some embodiments, the extension tube 28 may include a clamp 70, which may selectively close off the extension tube 28 to prevent blood or another fluid from flowing through the extension tube 28. In some embodiments, the clamp 70 may include a slide or pinch mechanism or another mechanism. In some embodiments, the system 64 may be integrated, having the integrated extension tube 28. In other embodiments, the system 64 may be non-integrated without the integrated extension tube 28.

In some embodiments, a needle assembly may be removably coupled to the proximal end 66 of the catheter adapter 14. In some embodiments, the needle assembly may include the needle hub 27 and the introducer needle 26 (illustrated, for example, in FIG. 1C). In some embodiments, the introducer needle 26 of the needle assembly may extend through the septum 18.

In some embodiments, an extension set 72 may be coupled to the proximal end 66 of the catheter adapter 14. In some embodiments, the proximal end 20 of the catheter adapter 14 may include a non-luer adapter corresponding to a non-luer adapter of the extension set 72. In some embodiments, the extension set 72 may include the introducer element 44, which may include a distal connector 74 coupled to the proximal end 66 of the catheter adapter 14, and a proximal connector 76.

In some embodiments, the distal connector 74 may be removably or non-removably coupled to the proximal end 66 of the catheter adapter 14. In some embodiments, the distal connector 74 may include one or more barbs, threading, adhesive, or another suitable coupling feature. As illustrated, in FIGS. 6A-6D, in some embodiments, the distal connector 74 and the proximal end 66 of the catheter adapter 14 may configured to be coupled together in a press-fit. In some embodiments, the distal connector 74 may include one or more arms 69, which may extend in a distal direction and contact an outer surface of the proximal end 66 of the catheter adapter 14. In some embodiments, the arms 69 may be locked to the outer surface of the proximal end 66 of the catheter adapter 14, such that the extension set 72 is non-removably coupled to the catheter adapter 14. For example, one or more of the arms 69 may include one or more inwardly-extending protrusions 71, which may each be aligned with and disposed within one or more grooves 73 of the catheter adapter 14 when the distal connector 74 is coupled to the proximal end 66 of the catheter adapter 14. As another example, one or more of the arms 69 may include one or more grooves, and the catheter adapter 14 may include one or more protrusions that may each be aligned with and disposed within the grooves.

In some embodiments, the distal connector 74 may include one or more wings 75, which may stabilize the introducer element 44 against skin of the patient. In some embodiments, a particular arm 69 may be disposed between two wings 75. In some embodiments, a bottom surface 77 of the wings 75 may smooth and/or parallel with the skin of the patient. In some embodiments, the wings 75 may stabilize the catheter adapter 14 and the catheter 12 at an appropriate insertion angle.

In some embodiments, the introducer element 44 may include the tube 54, which may be rigid. In some embodiments, the tube 54 may penetrate the septum 18 in response to the distal connector 74 being coupled to the proximal end 66 of the catheter adapter 14. In some embodiments, the septum 18 may be pre-slit prior to insertion of the introducer needle 26 and/or the tube 54 through the septum. In other embodiments, the tube 54 may create a slit in the septum 18 when the extension set 72 is coupled to the catheter adapter 14. In some embodiments, the tube 54 may be blunt. In some embodiments, the tube 54 may be constructed of plastic or metal, such as, for example, steel. In some embodiments, the tube 54 may include one or more flushing windows 80 through which fluid may travel. In some embodiments, a distal end of the tube 54 may be disposed proximate and/or within a wedge 79 securing the catheter 12.

In some embodiments, the extension set 72 may include tubing 78 disposed between the introducer element 44 and the proximal connector 76. In some embodiments, the tubing 78 may be flexible, which may reduce manipulation of an insertion site of the catheter 12 during further therapies. In some embodiments, the tubing 78 may include a clamp, which may selectively close off the tubing 78 to prevent blood or another fluid from flowing through the tubing 78. In some embodiments, the clamp may include a slide or pinch mechanism or another mechanism. In some embodiments, a distal end of the tubing 78 may be secured within the introducer element 44, and a proximal end of the tubing 78 may be secured within the proximal connector 76.

In some embodiments, the proximal end 66 of the catheter adapter 14 may be sealed with the septum 18 to ensure that fluid does not exit or leak out of the proximal end 66 of the catheter adapter 14. In some embodiments, the septum 18 may include or correspond to the septum of the Becton Dickinson NEXIVA™ Closed IV Catheter System or a similar septum. In some embodiments, the septum 18 may be formed from one piece. In some embodiments, the septum 18 may be formed from two pieces, a proximal piece and a distal piece. In some embodiments, the septum 18 may include a cavity to reduce drag when the introducer needle 26 is withdrawn through the septum 18 prior to attachment of the extension set 72.

In some embodiments, the septum 18 may include a slit. In further detail, in some embodiments the septum 18 may be pre-slit prior to insertion of the introducer needle 26 through the septum 18 or the slit may be formed when the introducer needle 26 is inserted through the septum 18. For example, in some embodiments, one or more of the proximal piece and the distal piece may be pre-slit to facilitate locating the introducer needle 26 therethrough, or one or more of the proximal piece and the distal piece may not be pre-slit but may instead may be slit when the introducer needle 26 is inserted therethrough. In some embodiments, the distal piece may provide the primary seal preventing fluid flow past the septum 18 while the proximal piece may provide a secondary seal.

In some embodiments, the septum 18 may be at least partially disposed within a canister 81, which may be secured within the catheter adapter 14 via a press-fit, snap-fit, threading, adhesive bonding, chemical bonding, ultrasonic welding, laser welding, or another suitable method. Suitable materials for the septum 18 may include a peroxide cured elastomer such as polyisoprene, silicone, and the like.

In some embodiments, the septum 18 may be constructed of one or more materials having a durometer in the range of 35-45 Shore A.

Figure 7A:
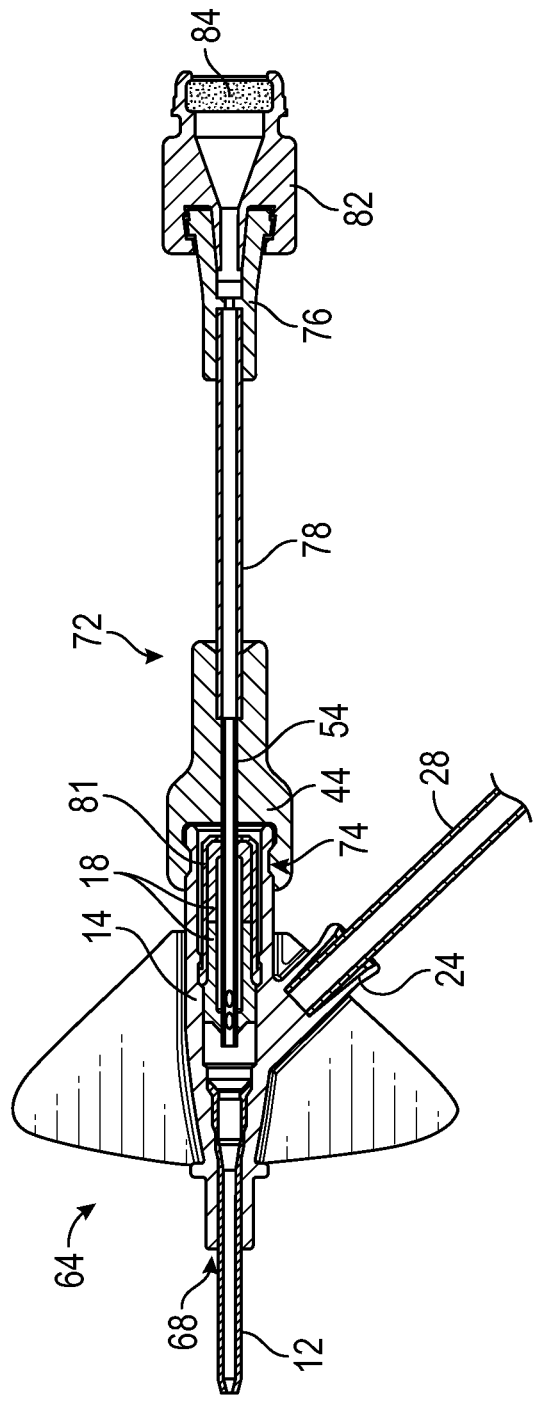
FIG. 7A is a cross-sectional view of another example extension set coupled with the catheter assembly of FIG. 6A, according to some embodiments.

Referring now to FIG. 7A, in some embodiments, the distal connector 74 of the introducer element 44 may include one or more protrusions that are coupled together with one or more grooves of the catheter adapter 14 with a snap fit. In some embodiments, the distal connector 74 of the introducer element 44 may include one or more grooves that are coupled together with one or more protrusions of the catheter adapter 14 with a snap fit. In some embodiments, the proximal connector 76 may include a luer adapter, such as, for example, a slip or thread male or female luer adapter, or a non-luer adapter. In some embodiments, a proximal end of the extension set 72 may include a single port, as illustrated, for example, in FIG. 7A. In other embodiments, the proximal end of the extension set 72 may include two or more ports.

In some embodiments, the proximal connector 76 may be coupled to a needleless connector 82, which may include a septum 84. In some embodiments, the needleless connector 82 may include a luer adapter, such as, for example, a slip or thread male or female luer adapter. Some non-limiting examples of needleless connectors are described in U.S. Pat. No. 8,066,670, filed Nov. 5, 2007, entitled "VASCULAR ACCESS DEVICE SEPTUM VENTING," which is hereby incorporated by reference. It is understood that the extension set 72 of FIG. 6A-6D may include one or more features of the extension set 72 of FIGS. 7A-7C. Also, it is understood that the extension set 72 of FIGS. 7A-7C may include one or more features of the extension set 72 of FIGS. 6A-6D.

Figure 7B:
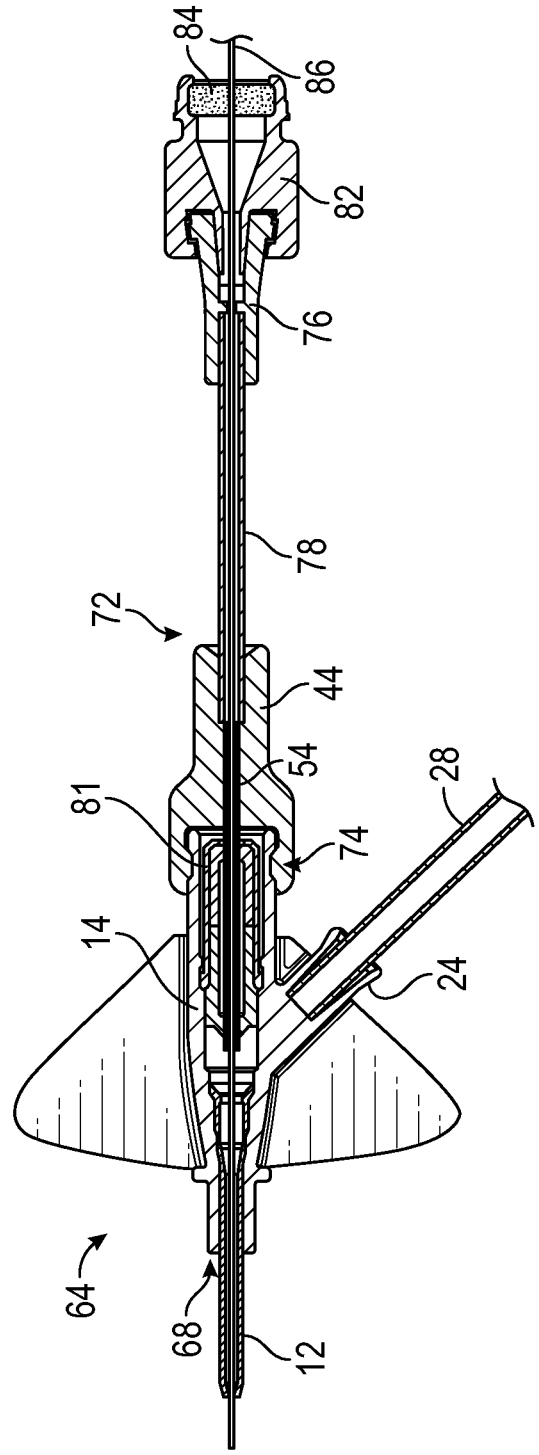
FIG. 7B is a cross-sectional view of the extension set and the catheter assembly of FIG. 7A having an example instrument extending therethrough, according to some embodiments.

Referring now to FIG. 7B, in some embodiments, the instrument 86 may be threaded distally through the extension set 72, the catheter adapter 14, and the catheter 12. In some embodiments, the instrument 86 may also be threaded through the needleless connector 82, as illustrated in FIG. 7B. As mentioned, in some embodiments, the instrument 86 may include an additional catheter for fluid infusion or blood draw, a guidewire, a probe with a sensor, or a light tube for disinfection. In some embodiments, the system 64 may form a straight or nearly straight pathway for delivery of the instrument 86 to the catheter 12. In some embodiments, the straight or nearly straight pathway may be smooth such that the instrument 86 is prevented from disturbance by any catches, such as any sharp edges or snag points.

Figure 7C:
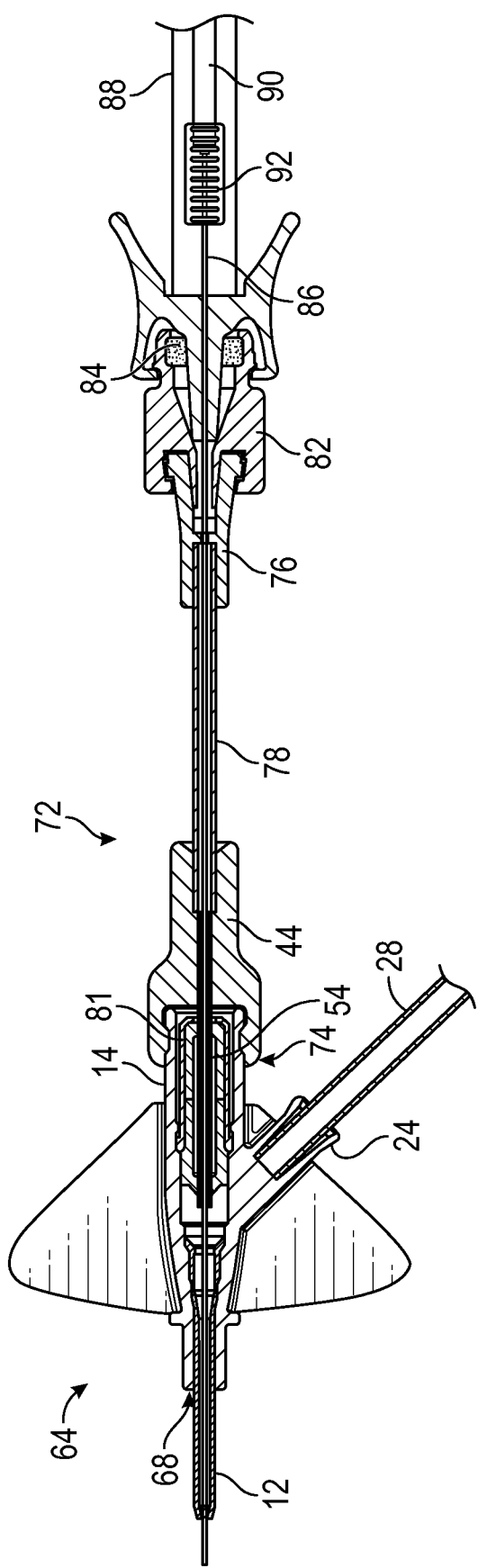
FIG. 7C is a cross-sectional view of the extension set and the catheter assembly of FIG. 7A, illustrating an example delivery device coupled to the extension set, according to some embodiments.

Referring now to FIG. 7C, in some embodiments, the system 64 may include an instrument delivery device 88, and the instrument 86 may be threaded through the system 64 via the instrument delivery device 64. In some embodiments, the instrument delivery device 88 may be removably coupled to the extension set 72 or the needleless connector 82. In some embodiments, the instrument delivery device 88 may include the instrument 86, which may be configured to advance distally through the septum 18 and into or through the catheter 12. In some embodiments, the instrument 86 may be advanced in response to movement along a slot 90 of an advancement tab 92 coupled to the instrument 86. Non-limiting examples of instrument delivery devices are described in U.S. Pat. No. 9,750,446, filed Feb. 4, 2013, entitled "SYSTEMS AND METHODS FOR PHLEBOTOMY THROUGH A PERIPHERAL IV CATHETER," and U.S. Patent Application No. 62/534,552, filed Jul. 19, 2017, entitled "EXTENSION HOUSING A PROBE OR INTRAVENOUS CATHETER," which are hereby incorporated by reference. In some embodiments, a blood collection device may be coupled to a proximal end of the instrument 86.

In some embodiments, after the introducer needle 26 is withdrawn and the needle hub 27 removed from the catheter adapter 14, the extension set 72 may be coupled to the proximal end 66 of the catheter adapter. In some embodiments, the instrument delivery device 88 may be coupled to the extension set, and the instrument 86 may be advanced distally until a distal end of the instrument 86 is disposed near or beyond a distal end of the catheter 12.

Figure 8:
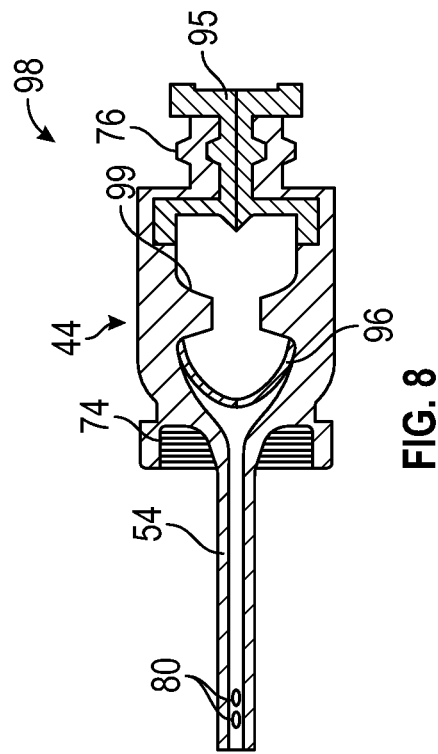
FIG. 8 is a cross-sectional view of another example introducer element, according to some embodiments.

Referring now to FIG. 8, in some embodiments, an extension set 98 may include a split septum 95 and/or an anti-reflux valve 96. In some embodiments, the anti-reflux valve 96 may be pre-slit. In some embodiments, the introducer element 44 of the extension set 98 may be coupled to the proximal end 66 of the catheter adapter 14. In some embodiments, the instrument 86 may be threaded through the introducer element 44, through the septum 18, and through the catheter 12 into the vasculature of the patient. In some embodiments, the instrument delivery device 88 may be coupled to the proximal connector 76 and used to thread the instrument 86 through the septum 18 and the catheter 12 into the vasculature of the patient. In some embodiments, a shape of an interior surface 99 of the introducer element 44 may be tapered in a distal direction to facilitate guidance of the instrument 86. In some embodiments, the extension set 98 may not include the tubing 78. In some embodiments, the anti-reflux valve may include any number of shapes and may be disposed at various locations in a fluid pathway of the extension set 98.

In some embodiments, the distal connector 74 may include a non-luer adapter, such as, for example, illustrated in FIG. 6 or 7, or a luer adapter, such as, for example, a slip or thread male or female luer adapter. In some embodiments, the extension set 98 may include or correspond to the extension set 72 of one or more the previous figures. In further detail, the extension set 98 may include one or more features of the extension set 72. In some embodiments, the extension set 72 may include one or more features of the extension set 98.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A system for facilitating instrument delivery through a peripheral intravenous catheter, the system comprising:
   a catheter assembly, comprising:
      a catheter adapter having a proximal end, a distal end, and a lumen extending through the proximal end of the catheter adapter and the distal end of the catheter adapter, the catheter adapter having a side port;
      an extension tube extending from the side port;
      a septum disposed in the lumen of the catheter adapter, wherein the septum comprises a first piece and a second piece disposed within a canister; and
      a peripheral intravenous catheter extending distally from the catheter adapter; and
   an extension set, comprising:
      a distal end comprising a distal connector and a rigid tube, wherein the rigid tube is rigid to form a straight pathway to facilitate delivery of an instrument through the rigid tube, wherein the distal connector is coupled to the proximal end of the catheter adapter, wherein the rigid tube penetrates the septum in response to the distal connector being coupled to the proximal end of the catheter adapter;
      a tapered portion, wherein the tapered portion is tapered inwardly in a distal direction to the rigid tube, wherein the tapered portion and the rigid tube are monolithically formed as a single unit, wherein the tapered portion is configured to guide the instrument distally into the rigid tube; and
      a proximal end comprising a proximal connector.

2. The system of claim 1, wherein the extension set further comprises tubing disposed between the distal connector and the proximal connector.

3. The system of claim 1, wherein the rigid tube is constructed of plastic or metal.

4. The system of claim 1, wherein a distal end of the rigid tube is blunt.

5. The system of claim 1, wherein the rigid tube comprises a plurality of flushing windows.

6. The system of claim 1, wherein the distal connector comprises a non-luer adapter.

7. The system of claim 1, wherein the distal connector is coupled to the proximal end of the catheter adapter with a snap-fit.

8. The system of claim 1, wherein the distal connector is coupled to the proximal end of the catheter adapter with a press-fit.

9. The system of claim 8, wherein the distal connector comprises a distally-extending arm that contacts an outer surface of the catheter adapter.

10. The system of claim 9, wherein the distally-extending arm is locked to the outer surface of the catheter adapter.

11. The system of claim 9, wherein the distal connector comprises a plurality of wings configured to contact skin of a patient and stabilize the system against skin of a patient.

12. The system of claim 1, further comprising a needleless connector coupled to the proximal connector.

13. The system of claim 1, further comprising the instrument disposed within the extension set and the catheter assembly, wherein the instrument comprises a guidewire, a probe with a sensor, tubing for fluid infusion or blood draw, or a light tube for disinfection.

14. The system of claim 1, wherein the distal end of the extension set comprises an anti-reflux valve.

15. An extension set for facilitating instrument delivery through a peripheral intravenous catheter, the extension set comprising:
   a distal end comprising a distal connector and a rigid tube having a blunt distal end, wherein the rigid tube is rigid to form a straight pathway to facilitate delivery of an instrument through the rigid tube, wherein the distal connector is configured to couple to a proximal end of a catheter adapter, wherein the distal connector comprises a non-luer adapter;
   a tapered portion, wherein the tapered portion is tapered inwardly in a distal direction to the rigid tube, wherein the tapered portion and the rigid tube are monolithically formed as a single unit, wherein the tapered portion is configured to guide the instrument distally into the rigid tube;
   a proximal end comprising a proximal connector; and
   a tubing disposed between the distal connector and the proximal connector.

16. The extension set of claim 15, wherein the distal connector is configured to be press-fit with the proximal end of the catheter adapter.

17. The extension set of claim 15, wherein the distal connector comprises a distally-extending arm that contacts an outer surface of the catheter adapter.

18. The extension set of claim 17, wherein the distally-extending arm is configured to lock to the outer surface of the catheter adapter.

19. The extension set of claim 17, wherein the distal connector comprises a plurality of wings configured to contact skin of a patient and stabilize the extension set against skin of a patient.

* * * * *